United States Patent
Chen et al.

(10) Patent No.: US 11,021,526 B2
(45) Date of Patent: Jun. 1, 2021

(54) DSG2-DERIVED PEPTIDES

(71) Applicant: Asclepiumm Taiwan Co., Ltd, New Taipei (TW)

(72) Inventors: Min-che Chen, New Taipei (TW); Chun-wei Chen, New Taipei (TW)

(73) Assignee: Asclepiumm Taiwan Co., Ltd, New Taipei (TW)

( * ) Notice: Subject to any disclaimer, the term of this patent is extended or adjusted under 35 U.S.C. 154(b) by 0 days.

(21) Appl. No.: 16/307,450

(22) PCT Filed: Jun. 6, 2017

(86) PCT No.: PCT/CN2017/087336
§ 371 (c)(1),
(2) Date: Dec. 5, 2018

(87) PCT Pub. No.: WO2017/211273
PCT Pub. Date: Dec. 14, 2017

(65) Prior Publication Data
US 2019/0177394 A1 Jun. 13, 2019

Related U.S. Application Data

(60) Provisional application No. 62/346,383, filed on Jun. 6, 2016.

(51) Int. Cl.
| | |
|---|---|
| *C07K 14/705* | (2006.01) |
| *A61P 35/00* | (2006.01) |
| *A61P 27/02* | (2006.01) |
| *C07K 7/06* | (2006.01) |
| *C07K 14/00* | (2006.01) |
| *A61K 9/00* | (2006.01) |
| *A61K 38/00* | (2006.01) |

(52) U.S. Cl.
CPC .......... *C07K 14/705* (2013.01); *A61K 9/0048* (2013.01); *A61P 27/02* (2018.01); *A61P 35/00* (2018.01); *C07K 7/06* (2013.01); *C07K 14/00* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,595,756 | A | * | 1/1997 | Bally .................. A61K 9/1272 264/4.1 |
| 2004/0229811 | A1 | | 11/2004 | Blaschuk et al. |
| 2012/0276082 | A1 | | 11/2012 | Chen |

FOREIGN PATENT DOCUMENTS

| | | |
|---|---|---|
| WO | 199957149 A2 | 11/1999 |
| WO | 2011036440 A1 | 3/2011 |
| WO | 2015165392 A1 | 11/2015 |

OTHER PUBLICATIONS

Zugazagoitia et al, Current Challenges in Cancer Treatment, Clinical Therapies, vol. 38, (2016), pp. 1551-1566 (Year: 2016).*
Sporn et at, "Chemoprevention of Cancer," Carcinogenesis, vol. 21 (2000), 525-530 (Year: 2000).*
Brennan, D. et al. "Increased expression of Dsg2 in malignant skin carcinomas." Cell Adhesion & Migration., vol. 3, No. 2, Jun. 30, 2009 (Jun. 30, 2009).
Giusti. B. et al. "Desmoglein-2-Integrin Beta-8 Interaction Regulates Actin Assembly in Endothelial Cells: Deregulation in Systemic Sclerosis." PLOS ONE., vol. 8, No. 7, Jul. 11, 2013 (Jul. 11, 2013).
Nava, P. et al. "Desmoglein-2: A Novel Regulator of Apoptosis in the Intestinal Epithelium." Molecular Biology of the Cell., vol. 18, Sep. 5, 2007 (Sep. 5, 2007).
Ota, T. et al. "No involvement of IgG autoantibodies against extracellular domains of desmoglein 2 in paraneoplastic pemphigus or inflammatory bowel diseases." Journal of Dermatological Science., vol. 32, No. 2, Aug. 31, 2003 (Aug. 31, 2003).
International Search Report dated Dec. 14, 2017 in corresponding International Application No. PCT/CN2017/087336, 6 pages.

* cited by examiner

*Primary Examiner* — Thomas S Heard
(74) *Attorney, Agent, or Firm* — Duane Morris LLP

(57) ABSTRACT

The invention provides Dsg2-derived peptides for inhibiting EMT and/or vasculogenic mimicry and treating and/or preventing angiogenesis-related diseases. Also provided are pharmaceutical compositions comprising the peptide of the invention and methods of using the peptide of the invention in inhibiting EMT and/or vasculogenic mimicry, and treating and/or preventing angiogenesis-related diseases.

24 Claims, 6 Drawing Sheets

Specification includes a Sequence Listing.

(A)

SEQ1: Dsg2 (aa 500-604)

(B)

(A)

(B)

(A)

(B)

(A)

(B)

(C)

(D)

(A)

(B)

SEQUENCE LISTING

```
<160> NUMBER OF SEQ ID NOS: 137

<210> SEQ ID NO 1
<211> LENGTH: 9
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa is A, T or S
<220> FEATURE:
<221> NAME/KEY: misc_feature
<222> LOCATION: (4)..(4)
<223> OTHER INFORMATION: Xaa is K, R or H
<220> FEATURE:
<221> NAME/KEY: misc_feature
<222> LOCATION: (6)..(6)
<223> OTHER INFORMATION: Xaa is K, R, N, H or Q
<220> FEATURE:
<221> NAME/KEY: misc_feature
<222> LOCATION: (8)..(8)
<223> OTHER INFORMATION: Xaa is A, V, I, G, L or P

<400> SEQUENCE: 1

Met Xaa Glu Xaa Trp Xaa Ile Xaa Arg
1               5

<210> SEQ ID NO 2
<211> LENGTH: 9
<212> TYPE: PRT
<213> ORGANISM: artificial sequence
<220> FEATURE:
<223> OTHER INFORMATION: synthetic peptide

<400> SEQUENCE: 2

Met Ala Glu Lys Trp Lys Ile Ala Arg
1               5

<210> SEQ ID NO 3
<211> LENGTH: 9
<212> TYPE: PRT
<213> ORGANISM: artificial sequence
<220> FEATURE:
<223> OTHER INFORMATION: synthetic peptide

<400> SEQUENCE: 3

Met Ala Glu Lys Trp Lys Ile Val Arg
1               5
```

```
<210> SEQ ID NO 4
<211> LENGTH: 9
<212> TYPE: PRT
<213> ORGANISM: artificial sequence
<220> FEATURE:
<223> OTHER INFORMATION: synthetic peptide

<400> SEQUENCE: 4

Met Ala Glu Lys Trp Lys Ile Ile Arg
1               5

<210> SEQ ID NO 5
<211> LENGTH: 9
<212> TYPE: PRT
<213> ORGANISM: artificial sequence
<220> FEATURE:
<223> OTHER INFORMATION: synthetic peptide

<400> SEQUENCE: 5

Met Ala Glu Lys Trp Arg Ile Ala Arg
1               5

<210> SEQ ID NO 6
<211> LENGTH: 9
<212> TYPE: PRT
<213> ORGANISM: artificial sequence
<220> FEATURE:
<223> OTHER INFORMATION: synthetic peptide

<400> SEQUENCE: 6

Met Ala Glu Lys Trp Arg Ile Val Arg
1               5

<210> SEQ ID NO 7
<211> LENGTH: 9
<212> TYPE: PRT
<213> ORGANISM: artificial sequence
<220> FEATURE:
<223> OTHER INFORMATION: synthetic peptide

<400> SEQUENCE: 7

Met Ala Glu Lys Trp Arg Ile Ile Arg
1               5

<210> SEQ ID NO 8
<211> LENGTH: 9
<212> TYPE: PRT
<213> ORGANISM: artificial sequence
<220> FEATURE:
<223> OTHER INFORMATION: synthetic peptide

<400> SEQUENCE: 8

Met Ala Glu Lys Trp Asn Ile Ala Arg
1               5

<210> SEQ ID NO 9
<211> LENGTH: 9
<212> TYPE: PRT
<213> ORGANISM: artificial sequence
<220> FEATURE:
<223> OTHER INFORMATION: synthetic peptide

<400> SEQUENCE: 9

Met Ala Glu Lys Trp Asn Ile Val Arg
1               5

<210> SEQ ID NO 10
```

```
<211> LENGTH: 9
<212> TYPE: PRT
<213> ORGANISM: artificial sequence
<220> FEATURE:
<223> OTHER INFORMATION: synthetic peptide

<400> SEQUENCE: 10

Met Ala Glu Lys Trp Asn Ile Ile Arg
1               5

<210> SEQ ID NO 11
<211> LENGTH: 9
<212> TYPE: PRT
<213> ORGANISM: artificial sequence
<220> FEATURE:
<223> OTHER INFORMATION: synthetic peptide

<400> SEQUENCE: 11

Met Ala Glu Arg Trp Lys Ile Ala Arg
1               5

<210> SEQ ID NO 12
<211> LENGTH: 9
<212> TYPE: PRT
<213> ORGANISM: artificial sequence
<220> FEATURE:
<223> OTHER INFORMATION: synthetic peptide

<400> SEQUENCE: 12

Met Ala Glu Arg Trp Lys Ile Val Arg
1               5

<210> SEQ ID NO 13
<211> LENGTH: 9
<212> TYPE: PRT
<213> ORGANISM: artificial sequence
<220> FEATURE:
<223> OTHER INFORMATION: synthetic peptide

<400> SEQUENCE: 13

Met Ala Glu Arg Trp Lys Ile Ile Arg
1               5

<210> SEQ ID NO 14
<211> LENGTH: 9
<212> TYPE: PRT
<213> ORGANISM: artificial sequence
<220> FEATURE:
<223> OTHER INFORMATION: synthetic peptide

<400> SEQUENCE: 14

Met Ala Glu Arg Trp Arg Ile Ala Arg
1               5

<210> SEQ ID NO 15
<211> LENGTH: 9
<212> TYPE: PRT
<213> ORGANISM: artificial sequence
<220> FEATURE:
<223> OTHER INFORMATION: synthetic peptide

<400> SEQUENCE: 15

Met Ala Glu Arg Trp Arg Ile Val Arg
1               5

<210> SEQ ID NO 16
<211> LENGTH: 9
```

```
<212> TYPE: PRT
<213> ORGANISM: artificial sequence
<220> FEATURE:
<223> OTHER INFORMATION: synthetic peptide

<400> SEQUENCE: 16

Met Ala Glu Arg Trp Arg Ile Ile Arg
1               5

<210> SEQ ID NO 17
<211> LENGTH: 9
<212> TYPE: PRT
<213> ORGANISM: artificial sequence
<220> FEATURE:
<223> OTHER INFORMATION: synthetic peptide

<400> SEQUENCE: 17

Met Ala Glu Arg Trp Asn Ile Ala Arg
1               5

<210> SEQ ID NO 18
<211> LENGTH: 9
<212> TYPE: PRT
<213> ORGANISM: artificial sequence
<220> FEATURE:
<223> OTHER INFORMATION: synthetic peptide

<400> SEQUENCE: 18

Met Ala Glu Arg Trp Asn Ile Val Arg
1               5

<210> SEQ ID NO 19
<211> LENGTH: 9
<212> TYPE: PRT
<213> ORGANISM: artificial sequence
<220> FEATURE:
<223> OTHER INFORMATION: synthetic peptide

<400> SEQUENCE: 19

Met Ala Glu Arg Trp Asn Ile Ile Arg
1               5

<210> SEQ ID NO 20
<211> LENGTH: 9
<212> TYPE: PRT
<213> ORGANISM: artificial sequence
<220> FEATURE:
<223> OTHER INFORMATION: synthetic peptide

<400> SEQUENCE: 20

Met Thr Glu Lys Trp Lys Ile Ala Arg
1               5

<210> SEQ ID NO 21
<211> LENGTH: 9
<212> TYPE: PRT
<213> ORGANISM: artificial sequence
<220> FEATURE:
<223> OTHER INFORMATION: synthetic peptide

<400> SEQUENCE: 21

Met Thr Glu Lys Trp Lys Ile Val Arg
1               5

<210> SEQ ID NO 22
<211> LENGTH: 9
<212> TYPE: PRT
```

```
<213> ORGANISM: artificial sequence
<220> FEATURE:
<223> OTHER INFORMATION: synthetic peptide

<400> SEQUENCE: 22

Met Thr Glu Lys Trp Lys Ile Ile Arg
1               5

<210> SEQ ID NO 23
<211> LENGTH: 9
<212> TYPE: PRT
<213> ORGANISM: artificial sequence
<220> FEATURE:
<223> OTHER INFORMATION: synthetic peptide

<400> SEQUENCE: 23

Met Thr Glu Lys Trp Arg Ile Ala Arg
1               5

<210> SEQ ID NO 24
<211> LENGTH: 9
<212> TYPE: PRT
<213> ORGANISM: artificial sequence
<220> FEATURE:
<223> OTHER INFORMATION: synthetic peptide

<400> SEQUENCE: 24

Met Thr Glu Lys Trp Arg Ile Val Arg
1               5

<210> SEQ ID NO 25
<211> LENGTH: 9
<212> TYPE: PRT
<213> ORGANISM: artificial sequence
<220> FEATURE:
<223> OTHER INFORMATION: synthetic peptide

<400> SEQUENCE: 25

Met Thr Glu Lys Trp Arg Ile Ile Arg
1               5

<210> SEQ ID NO 26
<211> LENGTH: 9
<212> TYPE: PRT
<213> ORGANISM: artificial sequence
<220> FEATURE:
<223> OTHER INFORMATION: synthetic peptide

<400> SEQUENCE: 26

Met Thr Glu Lys Trp Asn Ile Ala Arg
1               5

<210> SEQ ID NO 27
<211> LENGTH: 9
<212> TYPE: PRT
<213> ORGANISM: artificial sequence
<220> FEATURE:
<223> OTHER INFORMATION: synthetic peptide

<400> SEQUENCE: 27

Met Thr Glu Lys Trp Asn Ile Val Arg
1               5

<210> SEQ ID NO 28
<211> LENGTH: 9
<212> TYPE: PRT
<213> ORGANISM: artificial sequence
```

```
<220> FEATURE:
<223> OTHER INFORMATION: synthetic peptide

<400> SEQUENCE: 28

Met Thr Glu Lys Trp Asn Ile Ile Arg
1               5

<210> SEQ ID NO 29
<211> LENGTH: 9
<212> TYPE: PRT
<213> ORGANISM: artificial sequence
<220> FEATURE:
<223> OTHER INFORMATION: synthetic peptide

<400> SEQUENCE: 29

Met Thr Glu Arg Trp Lys Ile Ala Arg
1               5

<210> SEQ ID NO 30
<211> LENGTH: 9
<212> TYPE: PRT
<213> ORGANISM: artificial sequence
<220> FEATURE:
<223> OTHER INFORMATION: synthetic peptide

<400> SEQUENCE: 30

Met Thr Glu Arg Trp Lys Ile Val Arg
1               5

<210> SEQ ID NO 31
<211> LENGTH: 9
<212> TYPE: PRT
<213> ORGANISM: artificial sequence
<220> FEATURE:
<223> OTHER INFORMATION: synthetic peptide

<400> SEQUENCE: 31

Met Thr Glu Arg Trp Lys Ile Ile Arg
1               5

<210> SEQ ID NO 32
<211> LENGTH: 9
<212> TYPE: PRT
<213> ORGANISM: artificial sequence
<220> FEATURE:
<223> OTHER INFORMATION: synthetic peptide

<400> SEQUENCE: 32

Met Thr Glu Arg Trp Arg Ile Ala Arg
1               5

<210> SEQ ID NO 33
<211> LENGTH: 9
<212> TYPE: PRT
<213> ORGANISM: artificial sequence
<220> FEATURE:
<223> OTHER INFORMATION: synthetic peptide

<400> SEQUENCE: 33

Met Thr Glu Arg Trp Arg Ile Val Arg
1               5

<210> SEQ ID NO 34
<211> LENGTH: 9
<212> TYPE: PRT
<213> ORGANISM: artificial sequence
<220> FEATURE:
```

<223> OTHER INFORMATION: synthetic peptide

<400> SEQUENCE: 34

Met Thr Glu Arg Trp Arg Ile Ile Arg
1               5

<210> SEQ ID NO 35
<211> LENGTH: 9
<212> TYPE: PRT
<213> ORGANISM: artificial sequence
<220> FEATURE:
<223> OTHER INFORMATION: synthetic peptide

<400> SEQUENCE: 35

Met Thr Glu Arg Trp Asn Ile Ala Arg
1               5

<210> SEQ ID NO 36
<211> LENGTH: 9
<212> TYPE: PRT
<213> ORGANISM: artificial sequence
<220> FEATURE:
<223> OTHER INFORMATION: synthetic peptide

<400> SEQUENCE: 36

Met Thr Glu Arg Trp Asn Ile Val Arg
1               5

<210> SEQ ID NO 37
<211> LENGTH: 9
<212> TYPE: PRT
<213> ORGANISM: artificial sequence
<220> FEATURE:
<223> OTHER INFORMATION: synthetic peptide

<400> SEQUENCE: 37

Met Thr Glu Arg Trp Asn Ile Ile Arg
1               5

<210> SEQ ID NO 38
<211> LENGTH: 9
<212> TYPE: PRT
<213> ORGANISM: artificial sequence
<220> FEATURE:
<223> OTHER INFORMATION: synthetic peptide

<400> SEQUENCE: 38

Ala Ala Glu Lys Trp Lys Ile Ala Arg
1               5

<210> SEQ ID NO 39
<211> LENGTH: 9
<212> TYPE: PRT
<213> ORGANISM: artificial sequence
<220> FEATURE:
<223> OTHER INFORMATION: synthetic peptide

<400> SEQUENCE: 39

Met Ala Ala Lys Trp Lys Ile Ala Arg
1               5

<210> SEQ ID NO 40
<211> LENGTH: 9
<212> TYPE: PRT
<213> ORGANISM: artificial sequence
<220> FEATURE:
<223> OTHER INFORMATION: synthetic peptide

```
<400> SEQUENCE: 40

Met Ala Glu Ala Trp Lys Ile Ala Arg
1               5

<210> SEQ ID NO 41
<211> LENGTH: 9
<212> TYPE: PRT
<213> ORGANISM: artificial sequence
<220> FEATURE:
<223> OTHER INFORMATION: synthetic peptide

<400> SEQUENCE: 41

Met Ala Glu Lys Ala Lys Ile Ala Arg
1               5

<210> SEQ ID NO 42
<211> LENGTH: 9
<212> TYPE: PRT
<213> ORGANISM: artificial sequence
<220> FEATURE:
<223> OTHER INFORMATION: synthetic peptide

<400> SEQUENCE: 42

Met Ala Glu Lys Trp Ala Ile Ala Arg
1               5

<210> SEQ ID NO 43
<211> LENGTH: 9
<212> TYPE: PRT
<213> ORGANISM: artificial sequence
<220> FEATURE:
<223> OTHER INFORMATION: synthetic peptide

<400> SEQUENCE: 43

Met Ala Glu Lys Trp Lys Ala Ala Arg
1               5

<210> SEQ ID NO 44
<211> LENGTH: 9
<212> TYPE: PRT
<213> ORGANISM: artificial sequence
<220> FEATURE:
<223> OTHER INFORMATION: synthetic peptide

<400> SEQUENCE: 44

Met Ala Glu Lys Trp Lys Ile Ala Ala
1               5

<210> SEQ ID NO 45
<211> LENGTH: 14
<212> TYPE: PRT
<213> ORGANISM: artificial sequence
<220> FEATURE:
<223> OTHER INFORMATION: synthetic peptide

<400> SEQUENCE: 45

Met Ala Glu Lys Trp Lys Ile Ala Arg Gln Glu Ser Thr Ser
1               5                   10

<210> SEQ ID NO 46
<211> LENGTH: 13
<212> TYPE: PRT
<213> ORGANISM: artificial sequence
<220> FEATURE:
<223> OTHER INFORMATION: synthetic peptide
```

```
<400> SEQUENCE: 46

Met Ala Glu Lys Trp Lys Ile Ala Arg Gln Glu Ser Thr
1               5                   10

<210> SEQ ID NO 47
<211> LENGTH: 12
<212> TYPE: PRT
<213> ORGANISM: artificial sequence
<220> FEATURE:
<223> OTHER INFORMATION: synthetic peptide

<400> SEQUENCE: 47

Met Ala Glu Lys Trp Lys Ile Ala Arg Gln Glu Ser
1               5                   10

<210> SEQ ID NO 48
<211> LENGTH: 11
<212> TYPE: PRT
<213> ORGANISM: artificial sequence
<220> FEATURE:
<223> OTHER INFORMATION: synthetic peptide

<400> SEQUENCE: 48

Met Ala Glu Lys Trp Lys Ile Ala Arg Gln Glu
1               5                   10

<210> SEQ ID NO 49
<211> LENGTH: 10
<212> TYPE: PRT
<213> ORGANISM: artificial sequence
<220> FEATURE:
<223> OTHER INFORMATION: synthetic peptide

<400> SEQUENCE: 49

Met Ala Glu Lys Trp Lys Ile Ala Arg Gln
1               5                   10

<210> SEQ ID NO 50
<211> LENGTH: 8
<212> TYPE: PRT
<213> ORGANISM: artificial sequence
<220> FEATURE:
<223> OTHER INFORMATION: synthetic peptide

<400> SEQUENCE: 50

Met Ala Glu Lys Trp Lys Ile Ala
1               5

<210> SEQ ID NO 51
<211> LENGTH: 7
<212> TYPE: PRT
<213> ORGANISM: artificial sequence
<220> FEATURE:
<223> OTHER INFORMATION: synthetic peptide

<400> SEQUENCE: 51

Met Ala Glu Lys Trp Lys Ile
1               5

<210> SEQ ID NO 52
<211> LENGTH: 14
<212> TYPE: PRT
<213> ORGANISM: artificial sequence
<220> FEATURE:
<223> OTHER INFORMATION: synthetic peptide

<400> SEQUENCE: 52
```

Ala Glu Lys Trp Lys Ile Ala Arg Gln Glu Ser Thr Ser Val
1               5                   10

<210> SEQ ID NO 53
<211> LENGTH: 13
<212> TYPE: PRT
<213> ORGANISM: artificial sequence
<220> FEATURE:
<223> OTHER INFORMATION: synthetic peptide

<400> SEQUENCE: 53

Glu Lys Trp Lys Ile Ala Arg Gln Glu Ser Thr Ser Val
1               5                   10

<210> SEQ ID NO 54
<211> LENGTH: 12
<212> TYPE: PRT
<213> ORGANISM: artificial sequence
<220> FEATURE:
<223> OTHER INFORMATION: synthetic peptide

<400> SEQUENCE: 54

Lys Trp Lys Ile Ala Arg Gln Glu Ser Thr Ser Val
1               5                   10

<210> SEQ ID NO 55
<211> LENGTH: 11
<212> TYPE: PRT
<213> ORGANISM: artificial sequence
<220> FEATURE:
<223> OTHER INFORMATION: synthetic peptide

<400> SEQUENCE: 55

Trp Lys Ile Ala Arg Gln Glu Ser Thr Ser Val
1               5                   10

<210> SEQ ID NO 56
<211> LENGTH: 10
<212> TYPE: PRT
<213> ORGANISM: artificial sequence
<220> FEATURE:
<223> OTHER INFORMATION: synthetic peptide

<400> SEQUENCE: 56

Lys Ile Ala Arg Gln Glu Ser Thr Ser Val
1               5                   10

<210> SEQ ID NO 57
<211> LENGTH: 9
<212> TYPE: PRT
<213> ORGANISM: artificial sequence
<220> FEATURE:
<223> OTHER INFORMATION: synthetic peptide

<400> SEQUENCE: 57

Ile Ala Arg Gln Glu Ser Thr Ser Val
1               5

<210> SEQ ID NO 58
<211> LENGTH: 8
<212> TYPE: PRT
<213> ORGANISM: artificial sequence
<220> FEATURE:
<223> OTHER INFORMATION: synthetic peptide

<400> SEQUENCE: 58

```
Ala Arg Gln Glu Ser Thr Ser Val
1               5

<210> SEQ ID NO 59
<211> LENGTH: 7
<212> TYPE: PRT
<213> ORGANISM: artificial sequence
<220> FEATURE:
<223> OTHER INFORMATION: synthetic peptide

<400> SEQUENCE: 59

Arg Gln Glu Ser Thr Ser Val
1               5

<210> SEQ ID NO 60
<211> LENGTH: 13
<212> TYPE: PRT
<213> ORGANISM: artificial sequence
<220> FEATURE:
<223> OTHER INFORMATION: synthetic peptide

<400> SEQUENCE: 60

Ala Glu Lys Trp Lys Ile Ala Arg Gln Glu Ser Thr Ser
1               5                   10

<210> SEQ ID NO 61
<211> LENGTH: 11
<212> TYPE: PRT
<213> ORGANISM: artificial sequence
<220> FEATURE:
<223> OTHER INFORMATION: synthetic peptide

<400> SEQUENCE: 61

Glu Lys Trp Lys Ile Ala Arg Gln Glu Ser Thr
1               5                   10

<210> SEQ ID NO 62
<211> LENGTH: 9
<212> TYPE: PRT
<213> ORGANISM: artificial sequence
<220> FEATURE:
<223> OTHER INFORMATION: synthetic peptide

<400> SEQUENCE: 62

Lys Trp Lys Ile Ala Arg Gln Glu Ser
1               5

<210> SEQ ID NO 63
<211> LENGTH: 7
<212> TYPE: PRT
<213> ORGANISM: artificial sequence
<220> FEATURE:
<223> OTHER INFORMATION: synthetic peptide

<400> SEQUENCE: 63

Trp Lys Ile Ala Arg Gln Glu
1               5

<210> SEQ ID NO 64
<211> LENGTH: 9
<212> TYPE: PRT
<213> ORGANISM: artificial sequence
<220> FEATURE:
<223> OTHER INFORMATION: synthetic peptide

<400> SEQUENCE: 64

Met Ala Glu Lys Trp Lys Ile Ala Arg
```

<210> SEQ ID NO 65
<211> LENGTH: 11
<212> TYPE: PRT
<213> ORGANISM: artificial sequence
<220> FEATURE:
<223> OTHER INFORMATION: synthetic peptide

<400> SEQUENCE: 65

Cys Met Ala Glu Lys Trp Lys Ile Ala Arg Cys
1               5                   10

<210> SEQ ID NO 66
<211> LENGTH: 15
<212> TYPE: PRT
<213> ORGANISM: artificial sequence
<220> FEATURE:
<223> OTHER INFORMATION: synthetic peptide

<400> SEQUENCE: 66

Met Ala Glu Lys Trp Lys Ile Ala Arg Asp Asp Asp Asp Asp
1               5                   10                  15

<210> SEQ ID NO 67
<211> LENGTH: 17
<212> TYPE: PRT
<213> ORGANISM: artificial sequence
<220> FEATURE:
<223> OTHER INFORMATION: synthetic peptide

<400> SEQUENCE: 67

Cys Met Ala Glu Lys Trp Lys Ile Ala Arg Asp Asp Asp Asp Asp
1               5                   10                  15

Cys

<210> SEQ ID NO 68
<211> LENGTH: 12
<212> TYPE: PRT
<213> ORGANISM: artificial sequence
<220> FEATURE:
<223> OTHER INFORMATION: synthetic peptide

<400> SEQUENCE: 68

Arg Arg Arg Met Ala Glu Lys Trp Lys Ile Ala Arg
1               5                   10

<210> SEQ ID NO 69
<211> LENGTH: 13
<212> TYPE: PRT
<213> ORGANISM: artificial sequence
<220> FEATURE:
<223> OTHER INFORMATION: synthetic peptide

<400> SEQUENCE: 69

Arg Arg Arg Arg Met Ala Glu Lys Trp Lys Ile Ala Arg
1               5                   10

<210> SEQ ID NO 70
<211> LENGTH: 14
<212> TYPE: PRT
<213> ORGANISM: artificial sequence
<220> FEATURE:
<223> OTHER INFORMATION: synthetic peptide

<400> SEQUENCE: 70

```
Arg Arg Arg Arg Arg Met Ala Glu Lys Trp Lys Ile Ala Arg
1               5                   10
```

<210> SEQ ID NO 71
<211> LENGTH: 15
<212> TYPE: PRT
<213> ORGANISM: artificial sequence
<220> FEATURE:
<223> OTHER INFORMATION: synthetic peptide

<400> SEQUENCE: 71

```
Arg Arg Arg Arg Arg Arg Met Ala Glu Lys Trp Lys Ile Ala Arg
1               5                   10                  15
```

<210> SEQ ID NO 72
<211> LENGTH: 16
<212> TYPE: PRT
<213> ORGANISM: artificial sequence
<220> FEATURE:
<223> OTHER INFORMATION: synthetic peptide

<400> SEQUENCE: 72

```
Arg Arg Arg Arg Arg Arg Arg Met Ala Glu Lys Trp Lys Ile Ala Arg
1               5                   10                  15
```

<210> SEQ ID NO 73
<211> LENGTH: 12
<212> TYPE: PRT
<213> ORGANISM: artificial sequence
<220> FEATURE:
<223> OTHER INFORMATION: synthetic peptide

<400> SEQUENCE: 73

```
Met Ala Glu Lys Trp Lys Ile Ala Arg Asp Asp Asp
1               5                   10
```

<210> SEQ ID NO 74
<211> LENGTH: 15
<212> TYPE: PRT
<213> ORGANISM: artificial sequence
<220> FEATURE:
<223> OTHER INFORMATION: synthetic peptide

<400> SEQUENCE: 74

```
Arg Arg Arg Met Ala Glu Lys Trp Lys Ile Ala Arg Asp Asp Asp
1               5                   10                  15
```

<210> SEQ ID NO 75
<211> LENGTH: 16
<212> TYPE: PRT
<213> ORGANISM: artificial sequence
<220> FEATURE:
<223> OTHER INFORMATION: synthetic peptide

<400> SEQUENCE: 75

```
Arg Arg Arg Arg Met Ala Glu Lys Trp Lys Ile Ala Arg Asp Asp Asp
1               5                   10                  15
```

<210> SEQ ID NO 76
<211> LENGTH: 17
<212> TYPE: PRT
<213> ORGANISM: artificial sequence
<220> FEATURE:
<223> OTHER INFORMATION: synthetic peptide

<400> SEQUENCE: 76

```
Arg Arg Arg Arg Arg Met Ala Glu Lys Trp Lys Ile Ala Arg Asp Asp
```

```
1               5                  10                 15
Asp

<210> SEQ ID NO 77
<211> LENGTH: 18
<212> TYPE: PRT
<213> ORGANISM: artificial sequence
<220> FEATURE:
<223> OTHER INFORMATION: synthetic peptide

<400> SEQUENCE: 77

Arg Arg Arg Arg Arg Arg Met Ala Glu Lys Trp Lys Ile Ala Arg Asp
1               5                  10                 15

Asp Asp

<210> SEQ ID NO 78
<211> LENGTH: 19
<212> TYPE: PRT
<213> ORGANISM: artificial sequence
<220> FEATURE:
<223> OTHER INFORMATION: synthetic peptide

<400> SEQUENCE: 78

Arg Arg Arg Arg Arg Arg Arg Met Ala Glu Lys Trp Lys Ile Ala Arg
1               5                  10                 15

Asp Asp Asp

<210> SEQ ID NO 79
<211> LENGTH: 13
<212> TYPE: PRT
<213> ORGANISM: artificial sequence
<220> FEATURE:
<223> OTHER INFORMATION: synthetic peptide

<400> SEQUENCE: 79

Met Ala Glu Lys Trp Lys Ile Ala Arg Asp Asp Asp Asp
1               5                  10

<210> SEQ ID NO 80
<211> LENGTH: 16
<212> TYPE: PRT
<213> ORGANISM: artificial sequence
<220> FEATURE:
<223> OTHER INFORMATION: synthetic peptide

<400> SEQUENCE: 80

Arg Arg Arg Met Ala Glu Lys Trp Lys Ile Ala Arg Asp Asp Asp Asp
1               5                  10                 15

<210> SEQ ID NO 81
<211> LENGTH: 17
<212> TYPE: PRT
<213> ORGANISM: artificial sequence
<220> FEATURE:
<223> OTHER INFORMATION: synthetic peptide

<400> SEQUENCE: 81

Arg Arg Arg Arg Met Ala Glu Lys Trp Lys Ile Ala Arg Asp Asp Asp
1               5                  10                 15

Asp

<210> SEQ ID NO 82
<211> LENGTH: 18
<212> TYPE: PRT
```

```
<213> ORGANISM: artificial sequence
<220> FEATURE:
<223> OTHER INFORMATION: synthetic peptide

<400> SEQUENCE: 82

Arg Arg Arg Arg Arg Met Ala Glu Lys Trp Lys Ile Ala Arg Asp Asp
1               5                   10                  15

Asp Asp

<210> SEQ ID NO 83
<211> LENGTH: 19
<212> TYPE: PRT
<213> ORGANISM: artificial sequence
<220> FEATURE:
<223> OTHER INFORMATION: synthetic peptide

<400> SEQUENCE: 83

Arg Arg Arg Arg Arg Arg Met Ala Glu Lys Trp Lys Ile Ala Arg Asp
1               5                   10                  15

Asp Asp Asp

<210> SEQ ID NO 84
<211> LENGTH: 20
<212> TYPE: PRT
<213> ORGANISM: artificial sequence
<220> FEATURE:
<223> OTHER INFORMATION: synthetic peptide

<400> SEQUENCE: 84

Arg Arg Arg Arg Arg Arg Arg Met Ala Glu Lys Trp Lys Ile Ala Arg
1               5                   10                  15

Asp Asp Asp Asp
            20

<210> SEQ ID NO 85
<211> LENGTH: 14
<212> TYPE: PRT
<213> ORGANISM: artificial sequence
<220> FEATURE:
<223> OTHER INFORMATION: synthetic peptide

<400> SEQUENCE: 85

Met Ala Glu Lys Trp Lys Ile Ala Arg Asp Asp Asp Asp Asp
1               5                   10

<210> SEQ ID NO 86
<211> LENGTH: 17
<212> TYPE: PRT
<213> ORGANISM: artificial sequence
<220> FEATURE:
<223> OTHER INFORMATION: synthetic peptide

<400> SEQUENCE: 86

Arg Arg Arg Met Ala Glu Lys Trp Lys Ile Ala Arg Asp Asp Asp Asp
1               5                   10                  15

Asp

<210> SEQ ID NO 87
<211> LENGTH: 18
<212> TYPE: PRT
<213> ORGANISM: artificial sequence
<220> FEATURE:
<223> OTHER INFORMATION: synthetic peptide

<400> SEQUENCE: 87
```

Arg Arg Arg Arg Met Ala Glu Lys Trp Lys Ile Ala Arg Asp Asp
1               5                   10                  15

Asp Asp

<210> SEQ ID NO 88
<211> LENGTH: 19
<212> TYPE: PRT
<213> ORGANISM: artificial sequence
<220> FEATURE:
<223> OTHER INFORMATION: synthetic peptide

<400> SEQUENCE: 88

Arg Arg Arg Arg Arg Met Ala Glu Lys Trp Lys Ile Ala Arg Asp Asp
1               5                   10                  15

Asp Asp Asp

<210> SEQ ID NO 89
<211> LENGTH: 20
<212> TYPE: PRT
<213> ORGANISM: artificial sequence
<220> FEATURE:
<223> OTHER INFORMATION: synthetic peptide

<400> SEQUENCE: 89

Arg Arg Arg Arg Arg Arg Met Ala Glu Lys Trp Lys Ile Ala Arg Asp
1               5                   10                  15

Asp Asp Asp Asp
            20

<210> SEQ ID NO 90
<211> LENGTH: 21
<212> TYPE: PRT
<213> ORGANISM: artificial sequence
<220> FEATURE:
<223> OTHER INFORMATION: synthetic peptide

<400> SEQUENCE: 90

Arg Arg Arg Arg Arg Arg Arg Met Ala Glu Lys Trp Lys Ile Ala Arg
1               5                   10                  15

Asp Asp Asp Asp Asp
            20

<210> SEQ ID NO 91
<211> LENGTH: 15
<212> TYPE: PRT
<213> ORGANISM: artificial sequence
<220> FEATURE:
<223> OTHER INFORMATION: synthetic peptide

<400> SEQUENCE: 91

Met Ala Glu Lys Trp Lys Ile Ala Arg Asp Asp Asp Asp Asp Asp
1               5                   10                  15

<210> SEQ ID NO 92
<211> LENGTH: 18
<212> TYPE: PRT
<213> ORGANISM: artificial sequence
<220> FEATURE:
<223> OTHER INFORMATION: synthetic peptide

<400> SEQUENCE: 92

Arg Arg Arg Met Ala Glu Lys Trp Lys Ile Ala Arg Asp Asp Asp Asp
1               5                   10                  15

Asp Asp

<210> SEQ ID NO 93
<211> LENGTH: 19
<212> TYPE: PRT
<213> ORGANISM: artificial sequence
<220> FEATURE:
<223> OTHER INFORMATION: synthetic peptide

<400> SEQUENCE: 93

Arg Arg Arg Arg Met Ala Glu Lys Trp Lys Ile Ala Arg Asp Asp
1               5                   10                  15

Asp Asp Asp

<210> SEQ ID NO 94
<211> LENGTH: 20
<212> TYPE: PRT
<213> ORGANISM: artificial sequence
<220> FEATURE:
<223> OTHER INFORMATION: synthetic peptide

<400> SEQUENCE: 94

Arg Arg Arg Arg Arg Met Ala Glu Lys Trp Lys Ile Ala Arg Asp Asp
1               5                   10                  15

Asp Asp Asp Asp
            20

<210> SEQ ID NO 95
<211> LENGTH: 21
<212> TYPE: PRT
<213> ORGANISM: artificial sequence
<220> FEATURE:
<223> OTHER INFORMATION: synthetic peptide

<400> SEQUENCE: 95

Arg Arg Arg Arg Arg Arg Met Ala Glu Lys Trp Lys Ile Ala Arg Asp
1               5                   10                  15

Asp Asp Asp Asp Asp
            20

<210> SEQ ID NO 96
<211> LENGTH: 22
<212> TYPE: PRT
<213> ORGANISM: artificial sequence
<220> FEATURE:
<223> OTHER INFORMATION: synthetic peptide

<400> SEQUENCE: 96

Arg Arg Arg Arg Arg Arg Arg Met Ala Glu Lys Trp Lys Ile Ala Arg
1               5                   10                  15

Asp Asp Asp Asp Asp Asp
            20

<210> SEQ ID NO 97
<211> LENGTH: 12
<212> TYPE: PRT
<213> ORGANISM: artificial sequence
<220> FEATURE:
<223> OTHER INFORMATION: synthetic peptide

<400> SEQUENCE: 97

Asp Asp Asp Met Ala Glu Lys Trp Lys Ile Ala Arg
1               5                   10

<210> SEQ ID NO 98
<211> LENGTH: 13
<212> TYPE: PRT
<213> ORGANISM: artificial sequence
<220> FEATURE:
<223> OTHER INFORMATION: synthetic peptide

<400> SEQUENCE: 98

Asp Asp Asp Asp Met Ala Glu Lys Trp Lys Ile Ala Arg
1               5                   10

<210> SEQ ID NO 99
<211> LENGTH: 14
<212> TYPE: PRT
<213> ORGANISM: artificial sequence
<220> FEATURE:
<223> OTHER INFORMATION: synthetic peptide

<400> SEQUENCE: 99

Asp Asp Asp Asp Asp Met Ala Glu Lys Trp Lys Ile Ala Arg
1               5                   10

<210> SEQ ID NO 100
<211> LENGTH: 15
<212> TYPE: PRT
<213> ORGANISM: artificial sequence
<220> FEATURE:
<223> OTHER INFORMATION: synthetic peptide

<400> SEQUENCE: 100

Asp Asp Asp Asp Asp Asp Met Ala Glu Lys Trp Lys Ile Ala Arg
1               5                   10                  15

<210> SEQ ID NO 101
<211> LENGTH: 12
<212> TYPE: PRT
<213> ORGANISM: artificial sequence
<220> FEATURE:
<223> OTHER INFORMATION: synthetic peptide

<400> SEQUENCE: 101

Met Ala Glu Lys Trp Lys Ile Ala Arg Arg Arg Arg
1               5                   10

<210> SEQ ID NO 102
<211> LENGTH: 15
<212> TYPE: PRT
<213> ORGANISM: artificial sequence
<220> FEATURE:
<223> OTHER INFORMATION: synthetic peptide

<400> SEQUENCE: 102

Asp Asp Asp Met Ala Glu Lys Trp Lys Ile Ala Arg Arg Arg Arg
1               5                   10                  15

<210> SEQ ID NO 103
<211> LENGTH: 16
<212> TYPE: PRT
<213> ORGANISM: artificial sequence
<220> FEATURE:
<223> OTHER INFORMATION: synthetic peptide

<400> SEQUENCE: 103

Asp Asp Asp Asp Met Ala Glu Lys Trp Lys Ile Ala Arg Arg Arg Arg
1               5                   10                  15

<210> SEQ ID NO 104

```
<211> LENGTH: 17
<212> TYPE: PRT
<213> ORGANISM: artificial sequence
<220> FEATURE:
<223> OTHER INFORMATION: synthetic peptide

<400> SEQUENCE: 104

Asp Asp Asp Asp Asp Met Ala Glu Lys Trp Lys Ile Ala Arg Arg Arg
1               5                   10                  15

Arg

<210> SEQ ID NO 105
<211> LENGTH: 18
<212> TYPE: PRT
<213> ORGANISM: artificial sequence
<220> FEATURE:
<223> OTHER INFORMATION: synthetic peptide

<400> SEQUENCE: 105

Asp Asp Asp Asp Asp Asp Met Ala Glu Lys Trp Lys Ile Ala Arg Arg
1               5                   10                  15

Arg Arg

<210> SEQ ID NO 106
<211> LENGTH: 13
<212> TYPE: PRT
<213> ORGANISM: artificial sequence
<220> FEATURE:
<223> OTHER INFORMATION: synthetic peptide

<400> SEQUENCE: 106

Met Ala Glu Lys Trp Lys Ile Ala Arg Arg Arg Arg Arg
1               5                   10

<210> SEQ ID NO 107
<211> LENGTH: 16
<212> TYPE: PRT
<213> ORGANISM: artificial sequence
<220> FEATURE:
<223> OTHER INFORMATION: synthetic peptide

<400> SEQUENCE: 107

Asp Asp Asp Met Ala Glu Lys Trp Lys Ile Ala Arg Arg Arg Arg Arg
1               5                   10                  15

<210> SEQ ID NO 108
<211> LENGTH: 17
<212> TYPE: PRT
<213> ORGANISM: artificial sequence
<220> FEATURE:
<223> OTHER INFORMATION: synthetic peptide

<400> SEQUENCE: 108

Asp Asp Asp Asp Met Ala Glu Lys Trp Lys Ile Ala Arg Arg Arg Arg
1               5                   10                  15

Arg

<210> SEQ ID NO 109
<211> LENGTH: 18
<212> TYPE: PRT
<213> ORGANISM: artificial sequence
<220> FEATURE:
<223> OTHER INFORMATION: synthetic peptide

<400> SEQUENCE: 109
```

Asp Asp Asp Asp Asp Met Ala Glu Lys Trp Lys Ile Ala Arg Arg
1               5                   10                  15

Arg Arg

<210> SEQ ID NO 110
<211> LENGTH: 19
<212> TYPE: PRT
<213> ORGANISM: artificial sequence
<220> FEATURE:
<223> OTHER INFORMATION: synthetic peptide

<400> SEQUENCE: 110

Asp Asp Asp Asp Asp Met Ala Glu Lys Trp Lys Ile Ala Arg Arg
1               5                   10                  15

Arg Arg Arg

<210> SEQ ID NO 111
<211> LENGTH: 14
<212> TYPE: PRT
<213> ORGANISM: artificial sequence
<220> FEATURE:
<223> OTHER INFORMATION: synthetic peptide

<400> SEQUENCE: 111

Met Ala Glu Lys Trp Lys Ile Ala Arg Arg Arg Arg Arg Arg
1               5                   10

<210> SEQ ID NO 112
<211> LENGTH: 17
<212> TYPE: PRT
<213> ORGANISM: artificial sequence
<220> FEATURE:
<223> OTHER INFORMATION: synthetic peptide

<400> SEQUENCE: 112

Asp Asp Asp Met Ala Glu Lys Trp Lys Ile Ala Arg Arg Arg Arg
1               5                   10                  15

Arg

<210> SEQ ID NO 113
<211> LENGTH: 18
<212> TYPE: PRT
<213> ORGANISM: artificial sequence
<220> FEATURE:
<223> OTHER INFORMATION: synthetic peptide

<400> SEQUENCE: 113

Asp Asp Asp Asp Met Ala Glu Lys Trp Lys Ile Ala Arg Arg Arg
1               5                   10                  15

Arg Arg

<210> SEQ ID NO 114
<211> LENGTH: 19
<212> TYPE: PRT
<213> ORGANISM: artificial sequence
<220> FEATURE:
<223> OTHER INFORMATION: synthetic peptide

<400> SEQUENCE: 114

Asp Asp Asp Asp Asp Met Ala Glu Lys Trp Lys Ile Ala Arg Arg
1               5                   10                  15

Arg Arg Arg

```
<210> SEQ ID NO 115
<211> LENGTH: 20
<212> TYPE: PRT
<213> ORGANISM: artificial sequence
<220> FEATURE:
<223> OTHER INFORMATION: synthetic peptide

<400> SEQUENCE: 115

Asp Asp Asp Asp Asp Met Ala Glu Lys Trp Lys Ile Ala Arg Arg
1               5                   10                  15

Arg Arg Arg Arg
            20

<210> SEQ ID NO 116
<211> LENGTH: 15
<212> TYPE: PRT
<213> ORGANISM: artificial sequence
<220> FEATURE:
<223> OTHER INFORMATION: synthetic peptide

<400> SEQUENCE: 116

Met Ala Glu Lys Trp Lys Ile Ala Arg Arg Arg Arg Arg Arg Arg
1               5                   10                  15

<210> SEQ ID NO 117
<211> LENGTH: 18
<212> TYPE: PRT
<213> ORGANISM: artificial sequence
<220> FEATURE:
<223> OTHER INFORMATION: synthetic peptide

<400> SEQUENCE: 117

Asp Asp Asp Met Ala Glu Lys Trp Lys Ile Ala Arg Arg Arg Arg
1               5                   10                  15

Arg Arg

<210> SEQ ID NO 118
<211> LENGTH: 19
<212> TYPE: PRT
<213> ORGANISM: artificial sequence
<220> FEATURE:
<223> OTHER INFORMATION: synthetic peptide

<400> SEQUENCE: 118

Asp Asp Asp Asp Met Ala Glu Lys Trp Lys Ile Ala Arg Arg Arg
1               5                   10                  15

Arg Arg Arg

<210> SEQ ID NO 119
<211> LENGTH: 20
<212> TYPE: PRT
<213> ORGANISM: artificial sequence
<220> FEATURE:
<223> OTHER INFORMATION: synthetic peptide

<400> SEQUENCE: 119

Asp Asp Asp Asp Asp Met Ala Glu Lys Trp Lys Ile Ala Arg Arg
1               5                   10                  15

Arg Arg Arg Arg
            20

<210> SEQ ID NO 120
<211> LENGTH: 21
<212> TYPE: PRT
<213> ORGANISM: artificial sequence
```

```
<220> FEATURE:
<223> OTHER INFORMATION: synthetic peptide

<400> SEQUENCE: 120

Asp Asp Asp Asp Asp Asp Met Ala Glu Lys Trp Lys Ile Ala Arg Arg
1               5                   10                  15

Arg Arg Arg Arg Arg
            20

<210> SEQ ID NO 121
<211> LENGTH: 16
<212> TYPE: PRT
<213> ORGANISM: artificial sequence
<220> FEATURE:
<223> OTHER INFORMATION: synthetic peptide

<400> SEQUENCE: 121

Met Ala Glu Lys Trp Lys Ile Ala Arg Arg Arg Arg Arg Arg Arg Arg
1               5                   10                  15

<210> SEQ ID NO 122
<211> LENGTH: 19
<212> TYPE: PRT
<213> ORGANISM: artificial sequence
<220> FEATURE:
<223> OTHER INFORMATION: synthetic peptide

<400> SEQUENCE: 122

Asp Asp Asp Met Ala Glu Lys Trp Lys Ile Ala Arg Arg Arg Arg Arg
1               5                   10                  15

Arg Arg Arg

<210> SEQ ID NO 123
<211> LENGTH: 20
<212> TYPE: PRT
<213> ORGANISM: artificial sequence
<220> FEATURE:
<223> OTHER INFORMATION: synthetic peptide

<400> SEQUENCE: 123

Asp Asp Asp Asp Met Ala Glu Lys Trp Lys Ile Ala Arg Arg Arg Arg
1               5                   10                  15

Arg Arg Arg Arg
            20

<210> SEQ ID NO 124
<211> LENGTH: 21
<212> TYPE: PRT
<213> ORGANISM: artificial sequence
<220> FEATURE:
<223> OTHER INFORMATION: synthetic peptide

<400> SEQUENCE: 124

Asp Asp Asp Asp Asp Met Ala Glu Lys Trp Lys Ile Ala Arg Arg Arg
1               5                   10                  15

Arg Arg Arg Arg Arg
            20

<210> SEQ ID NO 125
<211> LENGTH: 22
<212> TYPE: PRT
<213> ORGANISM: artificial sequence
<220> FEATURE:
<223> OTHER INFORMATION: synthetic peptide
```

```
<400> SEQUENCE: 125

Asp Asp Asp Asp Asp Met Ala Glu Lys Trp Lys Ile Ala Arg Arg
1               5                   10                  15

Arg Arg Arg Arg Arg Arg
            20

<210> SEQ ID NO 126
<211> LENGTH: 15
<212> TYPE: PRT
<213> ORGANISM: artificial sequence
<220> FEATURE:
<223> OTHER INFORMATION: synthetic peptide

<400> SEQUENCE: 126

Ile Glu Pro Val Gln Thr Ile Cys His Asp Ala Glu Tyr Val Asn
1               5                   10                  15

<210> SEQ ID NO 127
<211> LENGTH: 15
<212> TYPE: PRT
<213> ORGANISM: artificial sequence
<220> FEATURE:
<223> OTHER INFORMATION: synthetic peptide

<400> SEQUENCE: 127

Ala Glu Tyr Val Asn Val Thr Ala Glu Asp Leu Asp Gly His Pro
1               5                   10                  15

<210> SEQ ID NO 128
<211> LENGTH: 15
<212> TYPE: PRT
<213> ORGANISM: artificial sequence
<220> FEATURE:
<223> OTHER INFORMATION: synthetic peptide

<400> SEQUENCE: 128

Leu Asp Gly His Pro Asn Ser Gly Pro Phe Ser Phe Ser Val Ile
1               5                   10                  15

<210> SEQ ID NO 129
<211> LENGTH: 15
<212> TYPE: PRT
<213> ORGANISM: artificial sequence
<220> FEATURE:
<223> OTHER INFORMATION: synthetic peptide

<400> SEQUENCE: 129

Ser Phe Ser Val Ile Asp Lys Pro Pro Gly Met Ala Glu Lys Trp
1               5                   10                  15

<210> SEQ ID NO 130
<211> LENGTH: 15
<212> TYPE: PRT
<213> ORGANISM: artificial sequence
<220> FEATURE:
<223> OTHER INFORMATION: synthetic peptide

<400> SEQUENCE: 130

Met Ala Glu Lys Trp Lys Ile Ala Arg Gln Glu Ser Thr Ser Val
1               5                   10                  15

<210> SEQ ID NO 131
<211> LENGTH: 15
<212> TYPE: PRT
<213> ORGANISM: artificial sequence
<220> FEATURE:
```

<223> OTHER INFORMATION: synthetic peptide

<400> SEQUENCE: 131

Glu Ser Thr Ser Val Leu Leu Gln Gln Ser Glu Lys Lys Leu Gly
1               5                   10                  15

<210> SEQ ID NO 132
<211> LENGTH: 15
<212> TYPE: PRT
<213> ORGANISM: artificial sequence
<220> FEATURE:
<223> OTHER INFORMATION: synthetic peptide

<400> SEQUENCE: 132

Glu Lys Lys Leu Gly Arg Ser Glu Ile Gln Phe Leu Ile Ser Asp
1               5                   10                  15

<210> SEQ ID NO 133
<211> LENGTH: 15
<212> TYPE: PRT
<213> ORGANISM: artificial sequence
<220> FEATURE:
<223> OTHER INFORMATION: synthetic peptide

<400> SEQUENCE: 133

Phe Leu Ile Ser Asp Asn Gln Gly Phe Ser Cys Pro Glu Lys Gln
1               5                   10                  15

<210> SEQ ID NO 134
<211> LENGTH: 15
<212> TYPE: PRT
<213> ORGANISM: artificial sequence
<220> FEATURE:
<223> OTHER INFORMATION: synthetic peptide

<400> SEQUENCE: 134

Cys Pro Glu Lys Gln Val Leu Thr Leu Thr Val Cys Glu Cys Leu
1               5                   10                  15

<210> SEQ ID NO 135
<211> LENGTH: 15
<212> TYPE: PRT
<213> ORGANISM: artificial sequence
<220> FEATURE:
<223> OTHER INFORMATION: synthetic peptide

<400> SEQUENCE: 135

Val Cys Glu Cys Leu His Gly Ser Gly Cys Arg Glu Ala Gln His
1               5                   10                  15

<210> SEQ ID NO 136
<211> LENGTH: 15
<212> TYPE: PRT
<213> ORGANISM: artificial sequence
<220> FEATURE:
<223> OTHER INFORMATION: synthetic peptide

<400> SEQUENCE: 136

Val Ser Thr Ser Glu Gln Arg Ala Ile Lys Trp Lys Glu Ala Met
1               5                   10                  15

<210> SEQ ID NO 137
<211> LENGTH: 105
<212> TYPE: PRT
<213> ORGANISM: artificial sequence
<220> FEATURE:
<223> OTHER INFORMATION: synthetic peptide

```
<400> SEQUENCE: 137

Ile Glu Pro Val Gln Thr Ile Cys His Asp Ala Glu Tyr Val Asn Val
1               5                   10                  15

Thr Ala Glu Asp Leu Asp Gly His Pro Asn Ser Gly Pro Phe Ser Phe
                20                  25                  30

Ser Val Ile Asp Lys Pro Pro Gly Met Ala Glu Lys Trp Lys Ile Ala
                35                  40                  45

Arg Gln Glu Ser Thr Ser Val Leu Leu Gln Gln Ser Glu Lys Lys Leu
            50                  55                  60

Gly Arg Ser Glu Ile Gln Phe Leu Ile Ser Asp Asn Gln Gly Phe Ser
65                  70                  75                  80

Cys Pro Glu Lys Gln Val Leu Thr Leu Thr Val Cys Glu Cys Leu His
                    85                  90                  95

Gly Ser Gly Cys Arg Glu Ala Gln His
                100                 105
```

DSG2-DERIVED PEPTIDES

CROSS-REFERENCE RELATED APPLICATIONS

This application is a 35 U.S.C. 371 National Phase Application of International Application PCT/CN2017/087336 filed on June 6, 2017, which claims the benefit of priority to U.S. provisional application 62/346,383 filed on Jun. 6, 2016, the disclosures of each of which are expressly incorporated herein by reference in their entirety.

FIELD OF THE INVENTION

The invention provides peptides for inhibiting vasculogenic mimicry and angiogenesis-related diseases. Particularly, the invention provides Dsg2-derived peptides and their applications in inhibition, prevention or treatment of vasculogenic mimicry and angiogenic dependent or angiogenic associated diseases.

BACKGROUND OF THE INVENTION

Desmosomes are one of the principal types of cell-cell adhesion junction between epithelial, myocardial and other tissues. Such desmosomes contain transmembrane glycoproteins called desmosomal cadherin, desmocollin (Dsc) and desmoglein (Dsg). Each occurs as at least three distinct genetic isoforms that show tissue-specific expression patterns.

Dsg2 are ubiquitously expressed in all tissues that form desmosomes. The extracellular domains of Dsg2 contain four cadherin repeat domains (EC1-4), each about 110 amino acids each in length. The extracellular repeat domain EC contains cell adhesion recognition (CAR) sites, which provide cell-cell adhesion. Therefore, Dsg2 has been identified to be a transmembrane cell adhesion molecule. Additionally, recent studies show that Dsg2 is not just a simple cell-cell adhesion molecule. Dsg2 is involved in promotion of angiogenesis, signaling of apoptosis, and is a substrate for MMPs.

Dsg2 has an important role in regulating EMT. They have shown that: (1) triggering EMT using hepatocyte growth factor/scattering factor (HGF/SF) shows that most of the desmosomal adhesion components are down-regulated, except Dsg2. (2) epithelial cells transfected with Dsg2 exhibit a mesenchymal-like morphology and show greater migration and invasion abilities under treatment by HGF/SF. (3) antibodies against EC2 domain of Dsg2 significantly block HGF/SF-induced EMT in vitro. Furthermore, the inventors have determined that antibodies to the EC2 domain of Dsg2 inhibit invasion of cancer cells, including MCF7 human breast cancer cells, LNCaP human prostate cancer cells, and KM12 human colon cancer cells. While not wishing to be bound to any particular theory, they propose that Dsg2 can function in the cell to promote EMT. US 20040229811 teaches cancer treatment by inhibiting adhesion of dsc- and/or dsg-expressing cells in a mammal. WO 99/57149 suggests that cell adhesion recognition (CAR) sites derived from the EC2 domain of Dsg2 can be used as modulating agents for treating cancer and/or inhibiting metastasis. US 20120276082 discloses an antagonist of Dsg2 wherein said antagonist modulates the function of the EC2 domain of Dsg2.

It has been implied that Dsg2 is involved in human diseases such as cancer, which Dsg2 is highly expressed in several epithelial-derived malignancies including basal cell carcinomas (BCC), squamous cell carcinomas (SCC), gastric cancer, melanoma, metastatic prostate cancer and bladder cancer.

SUMMARY OF THE INVENTION

The invention is based on the development of Dsg2-derived peptides for inhibiting EMT, having vasculogenic mimicry, and treating and/or preventing angiogenesis-related diseases. The peptides of the inventions may be derived from an amino acid residue from position 500 to 604 of Dsg2 (IEPVQTICHDA EYVNVTAEDL DGHPNSGPFS F SVIDKPPGMAEKWKIARQESTSVLLQQSEKKLGR-SEIQFLISDNQGF SCPEKQVLTLTVC ECLHGSGCREAQH (SEQ ID NO:137)) and they can be further modified.

The invention provides a synthetic peptide comprising an amino acid sequence of formula (I):

$$MX_1EX_2WX_3IX_4R \quad \text{(SEQ ID NO: 1)}$$

wherein
$X_1$ is A, T or S;
$X_2$ is K, R or H;
$X_3$ is K, R, N, H or Q; and
$X_4$ is A, V, I, G, L or P;
or a variant peptide thereof or a modified peptide thereof.

In some embodiments, in the formula (I), $X_1$ is A or T; $X_2$ is K or R; $X_3$ is K, R or N and X4 is A, V or I. In some further embodiments, the peptide of the invention comprises an amino acid sequence of any of SEQ ID NOs: 2 to 37.

In some embodiments, the variant peptide of the invention has at least 70%, 80%, 90%, 95%, 98%, 99% amino acid sequence identity with the sequence of SEQ ID NO: 1. In some embodiments, the variant peptides of the invention has one or more substitutions, deletions or insertions. In a further embodiment, the variant peptide of the invention has a conservative change.

In some embodiments, the variant peptide of the invention comprises an amino acid sequence selected from the group consisting of SEQ ID NOs: 45 to 63.

In some embodiments, the modified peptides of the invention may include, but are not limited to, one or more non-naturally occurring or modified amino acids, cyclic peptides and synthetic polyamino acid polymer (e.g., polylysine (polyK), poly L-aspartic acid (polyD), poly-L-arginine (polyR), poly L-glutamic acid (polyE) linked to the N-, C- or both N- and C-terminal of the peptides of the invention. In some embodiments, the modified peptide of the invention comprises an amino acid sequence selected from the group consisting of SEQ ID NOs: 64 to 67 and SEQ ID NOs: 68 to 125.

The invention also provides a synthetic peptide comprising an amino acid sequence selected from the group consisting of SEQ ID NOs: 126 to 135 or a variant peptide thereof or a modified peptide thereof. In one embodiment, the modified peptide is a reverse sequence of SEQ6, comprising an amino acid sequence of SEQ132: VSTSEQRAI-KWKEAM (SEQ ID NO: 136).

The invention also provides a pharmaceutical composition comprising a peptide of the invention or a variant peptide thereof or a modified peptide thereof.

The invention also provides a method inhibiting EMT and/or vasculogenic mimicry, and treating and/or preventing an angiogenic dependent or angiogenic associated disease in a subject, comprising administering a peptide of the invention or a peptide variant or a modified peptide thereof to the subject. Also, the invention provides a use of a peptide of the invention or a peptide variant or a modified peptide thereof in the manufacture of a medicament for inhibiting EMT and/or vasculogenic mimicry, and treating and/or preventing an angiogenic dependent or angiogenic associated disease in a subject.

DETAILED DESCRIPTION OF THE INVENTION

Figure 1:
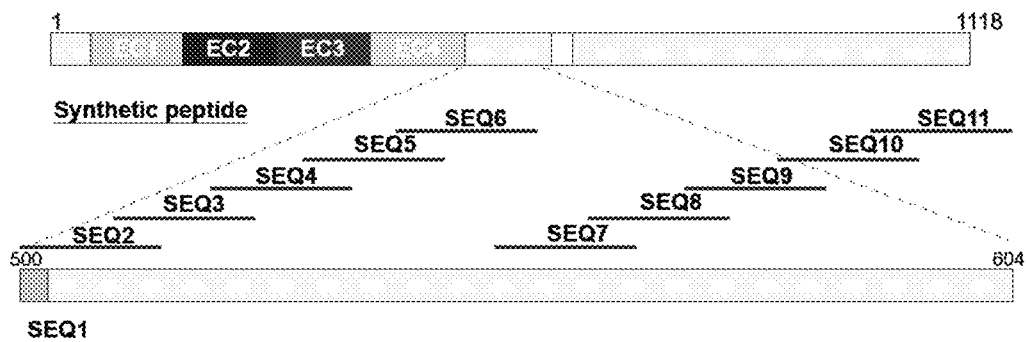
FIG. 1 (A) and (B) shows the EMT assay of the peptides of the invention. (A), The schematic diagram of the sequence-based design of SEQ2-SEQ11 from the Dsg2 extracellular domain aa500-604 (SEQ1). (B), HGF (hepatocyte growth factor) induced EMT (epithelial-mesenchymal transition) was inhibited by synthetic peptides, SEQ5, SEQ6, SEQ8, and SEQ10.
Figure 1:
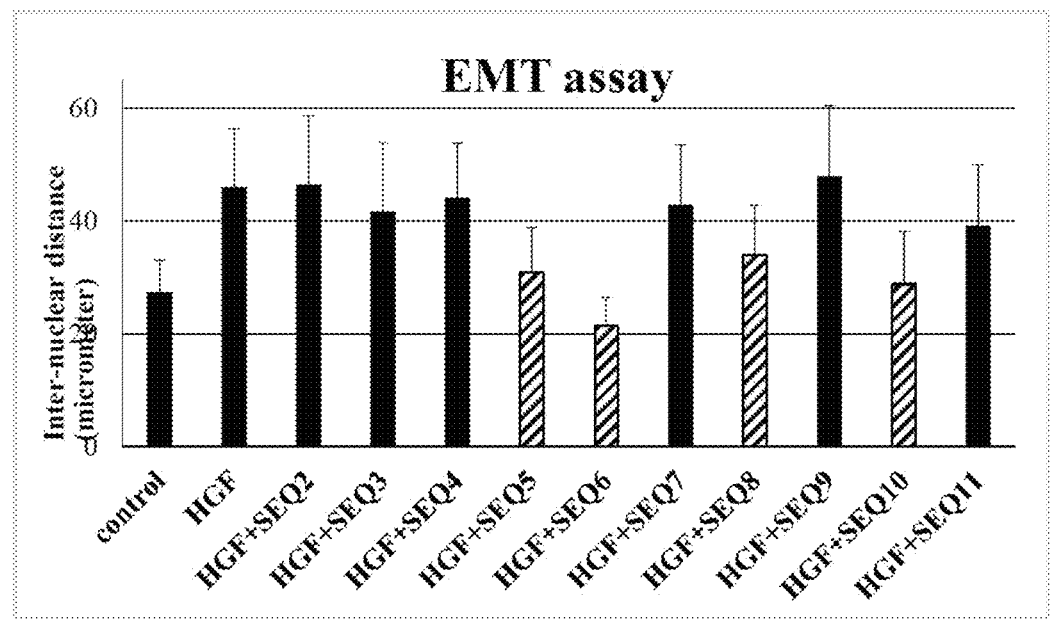

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

Throughout this application, the term "about" is used to indicate that a value includes the inherent variation of error.

As used herein, the phrase "synthetic peptide" for purposes of the present subject matter refers to a peptide prepared by a known chemical reaction of amino acids or by isolation and purification of a biological material as described above.

As used herein, the term "naturally-occurring" refers to the fact that an object can be found in nature. For example, a protein that is present in a source that can be isolated from a source in nature.

The term "administer," "administering" or "to administer" as used herein, refers to the giving or supplying of a medication, including in vivo administration, as well as administration directly to tissue ex vivo.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine: E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid that has been altered so as to increase the half-life of the peptide or to increase the potency of the peptide, or to increase the bioavailability of the peptide. The groups of amino acids that are conservative substitutions for one another are as follows.

Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

The term "peptide" as used herein, refers to a molecule of two or more amino acids chemically linked together. A peptide may refer to a polypeptide, protein or peptidomimetic. The peptides of the invention may comprise D-amino acids, a combination of D- and L-amino acids, and various "designer" amino acids (e.g., beta-methyl amino acids, C-alpha-methyl amino acids, and N-alpha-methyl amino acids, etc.) to convey special properties. Synthetic amino acids include omithine for lysine, and norleucine for leucine or isoleucine. In addition, the peptides can have peptidomimetic bonds, such as ester bonds, to prepare peptides with novel properties.

As used herein, the term "cyclic peptide mimetic" or "cyclic polypeptide mimetic" refers to a peptide mimetic that has as part of its structure one or more cyclic features such as a loop, bridging moiety, and/or an internal linkage.

As used herein, the term "pharmaceutically acceptable" refers to compounds and compositions which are suitable for administration to humans and/or animals without undue adverse side effects such as toxicity, irritation and/or allergic response commensurate with a reasonable benefit/risk ratio.

As used herein, the terms "subject" and "patient" are used interchangeably and will be understood to refer to a warm-blooded animal, particularly a mammal. Non-limiting examples of animals within the scope and meaning of this term include guinea pigs, dogs, cats, rats, mice, horses, goats, cattle, sheep, zoo animals, non-human primates, and humans.

As used herein, the term "effective amount" refers to an amount of a peptide compound sufficient to exhibit a detectable therapeutic effect without excessive adverse side effects (such as toxicity, irritation and allergic response) commensurate with a reasonable benefit/risk ratio when used in the manner of the inventive concepts.

As used herein, the term "therapeutically effective amount" refers to the amount of a subject Dsg2 peptide that, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject that may be predisposed to the disease but has not yet been diagnosed as having it; (b) inhibiting the disease, i.e., arresting its development; and (c) relieving the disease, i.e., causing regression of the disease.

In one aspect, the invention provides a synthetic peptide comprising an amino acid sequence of formula (I):

(SEQ ID NO: 1)

$$MX_1EX_2WX_3IX_4R$$

wherein $X_1$ is A, T or S;

$X_2$ is K, R or H;

$X_3$ is K, R, N, H or Q; and $X_4$ is A, V, I, G, L or P;

or a variant peptide thereof or a modified peptide thereof.

In some embodiments, in the formula (I), $X_1$ is A or T; $X_2$ is K or R; $X_3$ is K, R or N and X4 is A, V or I. In some further embodiments, the peptide of the invention comprises an amino acid sequence selected from the group consisting of:

| | | |
|---|---|---|
| SEQ17 | MAEKWKIAR | (SEQ ID NO: 2) |
| SEQ39 | MAEKWKIVR | (SEQ ID NO: 3) |
| SEQ40 | MAEKWKIIR | (SEQ ID NO: 4) |
| SEQ41 | MAEKWRIAR | (SEQ ID NO: 5) |
| SEQ42 | MAEKWRIVR | (SEQ ID NO: 6) |
| SEQ43 | MAEKWRIIR | (SEQ ID NO: 7) |

-continued

| | | |
|---|---|---|
| SEQ44 | MAEKWNIAR | (SEQ ID NO: 8) |
| SEQ45 | MAEKWNIVR | (SEQ ID NO: 9) |
| SEQ46 | MAEKWNIIR | (SEQ ID NO: 10) |
| SEQ47 | MAERWKIAR | (SEQ ID NO: 11) |
| SEQ48 | MAERWKIVR | (SEQ ID NO: 12) |
| SEQ49 | MAERWKIIR | (SEQ ID NO: 13) |
| SEQ50 | MAERWRIAR | (SEQ ID NO: 14) |
| SEQ51 | MAERWRIVR | (SEQ ID NO: 15) |
| SEQ52 | MAERWRIIR | (SEQ ID NO: 16) |
| SEQ53 | MAERWNIAR | (SEQ ID NO: 17) |
| SEQ54 | MAERWNIVR | (SEQ ID NO: 18) |
| SEQ55 | MAERWNIIR | (SEQ ID NO: 19) |
| SEQ56 | MTEKWKIAR | (SEQ ID NO: 20) |
| SEQ57 | MTEKWKIVR | (SEQ ID NO: 21) |
| SEQ58 | MTEKWKIIR | (SEQ ID NO: 22) |
| SEQ59 | MTEKWRIAR | (SEQ ID NO: 23) |
| SEQ60 | MTEKWRIVR | (SEQ ID NO: 24) |
| SEQ61 | MTEKWRIIR | (SEQ ID NO: 25) |
| SEQ62 | MTEKWNIAR | (SEQ ID NO: 26) |
| SEQ63 | MTEKWNIVR | (SEQ ID NO: 27) |
| SEQ64 | MTEKWNIIR | (SEQ ID NO: 28) |
| SEQ65 | MTERWKIAR | (SEQ ID NO: 29) |
| SEQ66 | MTERWKIVR | (SEQ ID NO: 30) |
| SEQ67 | MTERWKIIR | (SEQ ID NO: 31) |
| SEQ68 | MTERWRIAR | (SEQ ID NO: 32) |
| SEQ69 | MTERWRIVR | (SEQ ID NO: 33) |
| SEQ70 | MTERWRIIR | (SEQ ID NO: 34) |
| SEQ71 | MTERWNIAR | (SEQ ID NO: 35) |
| SEQ72 | MTERWNIVR | (SEQ ID NO: 36) |
| SEQ73 | MTERWNIIR | (SEQ ID NO: 37) |

In some embodiments, the variant peptide any of which amino acid residues may be changed from the corresponding residues of these peptides, while still encoding a peptide that maintains inhibitory activity on EMT, vasculogenic mimicry or angiogenesis-related diseases. In one embodiment, a variant of a peptide has at least 70%, 80%, 90%, 95%, 98%, 99% amino acid sequence identity with the sequence of SEQ ID NO: 1.

"Percent (%) amino acid sequence identity" is defined as the percentage of amino acid residues that are identical with amino acid residues in a reference (parent) polypeptide sequence when the two sequences are aligned. To determine % amino acid identity, sequences are aligned, and if necessary, gaps are introduced to achieve the maximum % sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

In some embodiments, peptide variants of the invention include variants in which residues at a particular position in the sequence have been substituted by other amino acids, and further include the possibility of inserting an additional residue or residues between two residues of the parent peptide/polypeptide as well as the possibility of deleting one or more residues from the parent sequence or adding one or more residues to the parent sequence. Any amino acid substitution, insertion, or deletion is encompassed by the invention. In certain circumstances, the substitution is a conservative substitution as described herein.

A conservative change generally leads to less change in the structure and function of the resulting protein. For example, the peptide of the present disclosure comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some further embodiments, the peptide variant (amino acid substitution) of the invention comprises an amino acid sequence selected from the group consisting of the following:

| SEQ32 | AAEKWKIAR | (SEQ ID NO: 38) |
| SEQ33 | MAAKWKIAR | (SEQ ID NO: 39) |
| SEQ34 | MAEAWKIAR | (SEQ ID NO: 40) |
| SEQ35 | MAEKAKIAR | (SEQ ID NO: 41) |
| SEQ36 | MAEKWAIAR | (SEQ ID NO: 42) |
| SEQ37 | MAEKWKAAR | (SEQ ID NO: 43) |
| SEQ38 | MAEKWKIAA | (SEQ ID NO: 44) |

In some further embodiments, the peptide variant (amino acid deletion) of the invention comprises an amino acid sequence selected from the group consisting of:

| SEQ12 | MAEKWKIARQESTS; | (SEQ ID NO: 45) |
| SEQ13 | MAEKWKIARQEST; | (SEQ ID NO: 46) |
| SEQ14 | MAEKWKIARQES; | (SEQ ID NO: 47) |
| SEQ15 | MAEKWKIARQE; | (SEQ ID NO: 48) |
| SEQ16 | MAEKWKIARQ; | (SEQ ID NO: 49) |
| SEQ18 | MAEKWKIA; | (SEQ ID NO: 50) |
| SEQ19 | MAEKWKI; | (SEQ ID NO: 51) |
| SEQ20 | AEKWKIARQESTSV; | (SEQ ID NO: 52) |
| SEQ21 | EKWKIARQESTSV; | (SEQ ID NO: 53) |
| SEQ22 | KWKIARQESTSV; | (SEQ ID NO: 54) |
| SEQ23 | WKIARQESTSV; | (SEQ ID NO: 55) |
| SEQ24 | KIARQESTSV; | (SEQ ID NO: 56) |
| SEQ25 | IARQESTSV; | (SEQ ID NO: 57) |
| SEQ26 | ARQESTSV; | (SEQ ID NO: 58) |
| SEQ27 | RQESTSV; | (SEQ ID NO: 59) |
| SEQ28 | AEKWKIARQESTS; | (SEQ ID NO: 60) |
| SEQ29 | EKWKIARQEST; | (SEQ ID NO: 61) |
| SEQ30 and | KWKIARQES; | (SEQ ID NO: 62) |
| SEQ31 | WKIARQE. | (SEQ ID NO: 63) |

In some embodiments, modified peptides of the invention may comprise one or more non-naturally occurring amino acids for modification. A "non-naturally occurring amino acid residue" refers to a residue, other than those naturally occurring amino acid residues, which is able to covalently bind adjacent amino acid residues(s) in a polypeptide chain. Non-natural amino acids include, but are not limited to, homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine.

In some embodiments, the modified peptide of the invention comprises an amino acid sequence selected from the group consisting of the following:

| MR9 DF: | MAEKWKIAR; | (SEQ ID NO: 64) |
| CMR9C DF: | CMAEKWKIARC; | (SEQ ID NO: 65) |
| MR9D6 DF: and | MAEKWKIARDDDDDD; | (SEQ ID NO: 66) |
| CMR9D6C DF: | CMAEKWKIARDDDDDDC. | (SEQ ID NO: 67) |

In one embodiment, the modified peptide is in a cyclic form. One modification is based on the cross-linking of amino acids to produce cyclic structures. Cyclic regions in a protein contain a rigid domain, which reduces conformational flexibility and degrees of rotational freedom, leading to very high affinity binding to target proteins. A number of methods for cyclizing a polypeptide are available to those skilled in the art and are incorporated herein by reference. Typically, the chemical reactivity of specific amino acid side chains and/or the carboxyl or amino termini of the polypeptide are exploited to crosslink two sites of the polypeptide to produce a cyclic molecule. In one method, the thiol groups of two cysteine residues are cross-linked by reaction with dibromoxylene.

In some embodiments, the modified peptide of the invention in cyclic form comprises an amino acid sequence selected from the group consisting of:

```
CMR9C DF:    CMAEKWKIARC;        (SEQ ID NO: 65)
and
CMR9D6C DF:  CMAEKWKIARDDDDDDC.  (SEQ ID NO: 67)
```

In another exemplary method, a side chain amino group and a terminal amino group are cross-linked with disuccinimidyl glutarate. In other approaches, cyclization is accomplished by making a thioether bridging group between two sites on the polypeptide. One chemical method relies on the incorporation of an N-chloroacetyl modified amino acid at the N-terminus of the polypeptide, followed by spontaneous reaction with the thiol side chain of an internal cysteine residue. An enzymatic method relies on the reaction between (1) a cysteine and (2) a dehydroalanine or dehydrobutyrine group, catalyzed by a lantibiotic synthetase, to create the thioether bridging group. The dehydro functional group can also be generated chemically by the oxidation of selenium containing amino acid side chains incorporated during translation.

In one embodiment, the modified peptide of the invention comprises a synthetic polyamino acid polymer (e.g., polylysine (polyK), poly L-aspartic acid (polyD), poly-L-arginine (polyR), poly L-glutamic acid (polyE) or polyglutamine (PolyQ) linked to the N-, C- or both N- and C-terminal of the peptide of the invention. In some embodiments, a modification to SEQ17 is made by adding poly-arginine (R) or poly-aspartic acid (D) to obtain a number of synthetic peptides SEQ74 to SEQ131. In a further embodiment, the synthetic polyamino acid comprises 1 to 12 polyamino acids, preferably 3 to 8 polyamino acids. In some embodiments, the synthetic polyamino acid comprises 1 to 12 K residues, 1 to 12 D residues, 1 to 12 R residues, 1 to 12 Q residues or 1 to 12 E residues or a combination thereof. In some embodiments, the synthetic polyamino acid comprises 3 to 7 R residues or 3 to 7 D residues or a combination thereof, the In some embodiments, the modified peptide is the peptide of the invention having a synthetic polyamino acid polymer selected from the group consisting of:

```
SEQ74    RRRMAEKWKIAR           (SEQ ID NO: 68)
SEQ75    RRRRMAEKWKIAR          (SEQ ID NO: 69)
SEQ76    RRRRRMAEKWKIAR         (SEQ ID NO: 70)
SEQ77    RRRRRRMAEKWKIAR        (SEQ ID NO: 71)
SEQ78    RRRRRRRMAEKWKIAR       (SEQ ID NO: 72)
SEQ79    MAEKWKIARDDD           (SEQ ID NO: 73)
SEQ80    RRRMAEKWKIARDDD        (SEQ ID NO: 74)
SEQ81    RRRRMAEKWKIARDDD       (SEQ ID NO: 75)
SEQ82    RRRRRMAEKWKIARDDD      (SEQ ID NO: 76)
SEQ83    RRRRRRMAEKWKIARDDD     (SEQ ID NO: 77)
SEQ84    RRRRRRRMAEKWKIARDDD    (SEQ ID NO: 78)
SEQ85    MAEKWKIARDDDD          (SEQ ID NO: 79)
SEQ86    RRRMAEKWKIARDDDD       (SEQ ID NO: 80)
SEQ87    RRRRMAEKWKIARDDDD      (SEQ ID NO: 81)
SEQ88    RRRRRMAEKWKIARDDDD     (SEQ ID NO: 82)
SEQ89    RRRRRRMAEKWKIARDDDD    (SEQ ID NO: 83)
SEQ90    RRRRRRRMAEKWKIARDDDD   (SEQ ID NO: 84)
SEQ91    MAEKWKIARDDDDD         (SEQ ID NO: 85)
SEQ92    RRRMAEKWKIARDDDDD      (SEQ ID NO: 86)
SEQ93    RRRRMAEKWKIARDDDDD     (SEQ ID NO: 87)
SEQ94    RRRRRMAEKWKIARDDDDD    (SEQ ID NO: 88)
SEQ95    RRRRRRMAEKWKIARDDDDD   (SEQ ID NO: 89)
SEQ96    RRRRRRRMAEKWKIARDDDDD  (SEQ ID NO: 90)
SEQ97    MAEKWKIARDDDDDD        (SEQ ID NO: 91)
SEQ98    RRRMAEKWKIARDDDDDD     (SEQ ID NO: 92)
SEQ99    RRRRMAEKWKIARDDDDDD    (SEQ ID NO: 93)
SEQ100   RRRRRMAEKWKIARDDDDDD   (SEQ ID NO: 94)
SEQ101   RRRRRRMAEKWKIARDDDDDD  (SEQ ID NO: 95)
SEQ102   RRRRRRRMAEKWKIARDDDDDD (SEQ ID NO: 96)
SEQ103   DDDMAEKWKIAR           (SEQ ID NO: 97)
SEQ104   DDDDMAEKWKIAR          (SEQ ID NO: 98)
SEQ105   DDDDDMAEKWKIAR         (SEQ ID NO: 99)
SEQ106   DDDDDDMAEKWKIAR        (SEQ ID NO: 100)
SEQ107   MAEKWKIARRRR           (SEQ ID NO: 101)
SEQ108   DDDMAEKWKIARRRR        (SEQ ID NO: 102)
SEQ109   DDDDMAEKWKIARRRR       (SEQ ID NO: 103)
SEQ110   DDDDDMAEKWKIARRRR      (SEQ ID NO: 104)
SEQ111   DDDDDDMAEKWKIARRRR     (SEQ ID NO: 105)
SEQ112   MAEKWKIARRRRR          (SEQ ID NO: 106)
SEQ113   DDDMAEKWKIARRRRR       (SEQ ID NO: 107)
SEQ114   DDDDMAEKWKIARRRRR      (SEQ ID NO: 108)
SEQ115   DDDDDMAEKWKIARRRRR     (SEQ ID NO: 109)
SEQ116   DDDDDDMAEKWKIARRRRR    (SEQ ID NO: 110)
SEQ117   MAEKWKIARRRRRR         (SEQ ID NO: 111)
SEQ118   DDDMAEKWKIARRRRRR      (SEQ ID NO: 112)
SEQ119   DDDDMAEKWKIARRRRRR     (SEQ ID NO: 113)
SEQ120   DDDDDMAEKWKIARRRRRR    (SEQ ID NO: 114)
```

-continued

| SEQ121 | DDDDDDMAEKWKIARRRRRR | (SEQ ID NO: 115) |
| --- | --- | --- |
| SEQ122 | MAEKWKIARRRRRRR | (SEQ ID NO: 116) |
| SEQ123 | DDDMAEKWKIARRRRRRR | (SEQ ID NO: 117) |
| SEQ124 | DDDDMAEKWKIARRRRRRR | (SEQ ID NO: 118) |
| SEQ125 | DDDDDMAEKWKIARRRRRRR | (SEQ ID NO: 119) |
| SEQ126 | DDDDDDMAEKWKIARRRRRRR | (SEQ ID NO: 120) |
| SEQ127 | MAEKWKIARRRRRRRR | (SEQ ID NO: 121) |
| SEQ128 | DDDMAEKWKIARRRRRRRR | (SEQ ID NO: 122) |
| SEQ129 | DDDDMAEKWKIARRRRRRRR | (SEQ ID NO: 123) |
| SEQ130 | DDDDDMAEKWKIARRRRRRRR | (SEQ ID NO: 124) |
| SEQ131 | DDDDDDMAEKWKIARRRRRRRR | (SEQ ID NO: 125) |

In another aspect, the invention provides a synthetic peptide comprising an amino acid sequence selected from the group consisting of the following:

| SEQ2 | IEPVQTICHDAEYVN; | (SEQ ID NO: 126) |
| --- | --- | --- |
| SEQ3 | AEYVNVTAEDLDGHP; | (SEQ ID NO: 127) |
| SEQ4 | LDGHPNSGPFSFSVI; | (SEQ ID NO: 128) |
| SEQ5 | SFSVIDKPPGMAEKW; | (SEQ ID NO: 129) |
| SEQ6 | MAEKWMIARQESTSV; | (SEQ ID NO: 130) |
| SEQ7 | ESTSVLLQQSEKKLG; | (SEQ ID NO: 131) |
| SEQ8 | EKKLGRSEIQFLISD; | (SEQ ID NO: 132) |
| SEQ9 | FLISDNQGFSCPEKQ; | (SEQ ID NO: 133) |
| SEQ10 and | CPEKQVLTLTVCECL; | (SEQ ID NO: 134) |
| SEQ11 | VCECLHGSGCREAQH. | (SEQ ID NO: 135) | or a variant peptide thereof or a modified peptide thereof.

In one embodiment, the modified peptide is a reverse sequence of SEQ6, comprising an amino acid sequence of SEQ132: VSTSEQRAIKWKEAM (SEQ ID NO: 136).

The variant peptide of SEQ2 to SEQ11 includes a peptide having amino acid sequence identity as described herein and amino acid substitution, addition or deletion as described herein. The modified peptide includes a peptide with non-naturally occurring amino acid modification, cyclic modification and synthetic polyamino acid polymer modification.

The peptides of the inventions may be derived from an amino acid residue from position 500 to 604 of Dsg2 (IEPVQTICHDA EYVNVTAEDL DGHPNSGPFS FSVIDKPPGM AEKWKIARQESTSVLLQQSEKKLGR-SEIQFLISDNQGFSCPEKQVLTLTVCECLHGSGCR EAQH (SEQ ID NO:137)) and they can be further modified. The presently described peptides may also be prepared by chemical synthesis or manufacture using recombinant DNA technology. For example, the peptides can be obtained by methods using azide, acid chloride, acid anhydride, compound acid anhydride, DCC, activated ester, Woodward's reagent K, carbonylimidazole, deoxidixation, DCC/HONB, BOP reagent, etc., as known in the art. Also, they can be prepared by chemical synthesis using an automated peptide synthesizer.

Following such a chemical reaction, the peptides can be separated and purified by a known purification method. An example of such purification methods can include a combination of solvent extraction, distillation, column chromatography, liquid chromatography, recrystallization and the like.

Further, recombinant expression systems in host cells (such as *E. coli*) may be used to express the presently described peptides as fusion proteins, with a specific enzymatic cleavage site, for example, enterokinase. Next, the cells are broken and centrifuged and the resulting soup contains the peptide. The peptide can then be loaded on a specific affinity column, for example, a Ni2+ or glutathione column, to be eluted. After elution, the purified peptide is subjected to a specific enzymatic cleavage reaction. Then, the peptide is purified from the resultant mixture by HPLC or ion exchange chromatography. Methods involving conventional and analytical chemistry, molecular biological and cell biological techniques are described in detail in many publicly known references.

In another aspect, the invention provides a pharmaceutical composition comprising a peptide of the invention or a variant peptide thereof or a modified peptide thereof.

The present disclosure provides pharmaceutical compositions capable of inhibiting EMT, having vasculogenic mimicry, and treating and/or preventing an angiogenic dependent or angiogenic associated disease, comprising a peptide of the invention or a variant peptide thereof or a modified peptide thereof and at least one pharmaceutically acceptable carrier, diluent, or excipient. The peptide of the invention is preferably combined with other components such as a carrier in a composition such as a pharmaceutical composition. The compositions are useful when administered in methods of medical treatment or prevention of angiogenesis-related diseases. Pharmaceutically acceptable carriers, excipients, or stabilizers are nontoxic to recipients at the dosages and concentrations employed. They can be solid, semi-solid, or liquid. The pharmaceutical compositions of the present invention can be in the form of tablets, pills, powders, lozenges, sachets, cachets, elixirs, suspensions, emulsions, solutions, or syrups.

In some embodiments, the present invention provides a method inhibiting EMT and/or vasculogenic mimicry, and treating and/or preventing an angiogenic dependent or angiogenic associated disease in a subject, comprising administering a peptide of the invention or a peptide variant or a modified peptide thereof to the subject. Accordingly, the invention provides a use of a peptide of the invention or a peptide variant or a modified peptide thereof in the manufacture of a medicament for inhibiting EMT and/or vasculogenic mimicry, and treating and/or preventing an angiogenic dependent or angiogenic associated disease in a subject.

Angiogenesis is used throughout the specification to describe biological processes which result in the development of blood vessels or increase in the vascularity of tissue in an organism. Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases or disorders treated, ameliorated or prevented by the instant invention include the following: macular degeneration, age-Related macular degeneration, neoplasia, internal malignancies such as eye or ocular cancer, rectal cancer, colon cancer, cervical cancer, prostate cancer, breast cancer and bladder cancer, benign and malignant rumors, including various cancers such as, anal and oral cancers, stomach, rectal, liver, pancreatic, lung, cervix uteri, corpus uteri, ovary, prostate, testis, renal, mouth/pharynx, esophageal, larynx, kidney, brain/ens (e.g., gliomas), head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, lymphoma, neurofibromatosis, tuberous sclerosis (each of which conditions produces benign tumors of the skin), hemangiomas, lymphangiogenesis, rhabdomyosarcomas, retinoblastoma, osteosarcoma, acoustic neuroma, neurofibroma, trachoma, pyogenic granulomas, blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen, psoriasis, acne, rosacea warts, eczema, neurofibromatosis, Sturge-Weber syndrome, venous ulcers of the skin, tuberous sclerosis, chronic inflammatory disease, arthritis, lupus, scleroderma, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium, keratitis sicca, Sjogren's, phylectenulosis, syphilis, Mycobacteria infections, lipid degeneration, chemical burns, bacterial ulcers, fungal ulcers, herpes simplex infections, herpes zoster infections, protozoan infections, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, diabetic retinopathy, macular edema, macular degeneration, sickle cell anemia, sarcoid, pseudoxanthoma elasticum, Pagefs disease, vein occlusion, artery occlusion, carotid obstructive disease, chronic uveitis/vitritis, Lyme disease, systemic lupus erythematosus, Bales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, rubeosis (neovascularization of the ankle), diseases caused by the abnormal proliferation of fibrovascular or fibrous tissue including all forms of proliferative vitreoretinopathy, whether or not associated with diabetes, neovascular disease, pannus, diabetic macular edema, vascular retinopathy, retinal degeneration, inflammatory diseases of the retina, proliferative vitreoretinopathy, diseases associated with rubeosis (neovascularization of the ankle), diseases caused by the abnormal proliferation of fibrovascular or fibrous tissue including all forms of proliferative vitreoretinopathy, Crohn's disease and ulcerative colitis, sarcoidosis, osteoarthritis, inflammatory bowel diseases, skin lesions, Osler-Weber-Rendu disease, or hereditary hemorrhagic telangiectasia, osteoarthritis, Sarcoidosis, skin lesions, acquired immune deficiency syndrome, and small bowel obstruction.

In some embodiment, the angiogenic dependent or angiogenic associated disease is neoplasia (including a malignant tumor or cancer), macular degeneration (including age-Related macular degeneration), neovascular disease, vascular retinopathy or retinal degeneration.

Angiogenesis inhibiting peptides of the present invention are used to treat, ameliorate or prevent benign and malignant tumors, including various cancers such as, cervical cancer, anal cancer, oral cancer, stomach cancer, colon cancer, bladder cancer, rectal cancer, liver cancer, pancreatic cancer, lung cancer, breast cancer, cervix uteri cancer, corpus uteri cancer, ovary cancer, prostate cancer, testis cancer, renal cancer, brain cancer (e.g., gliomas), head and neck cancer, eye or ocular cancer, throat cancer, melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Angiogenesis is prominent in solid tumor formation and metastasis.

Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow mat give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenic disease, angiogenic disorder and angiogenic skin disorder are used throughout the specification to describe a disorder, generally a skin disorder or related disorder which occurs as a consequence of or which results in increased vascularization in tissue. Any skin disorder which has as a primary or secondary characterization, increased vascularization, is considered an angiogenic skin disorder for purposes of the present invention and is amenable to treatment with compounds according to the present invention.

Methods for treating, ameliorating, or preventing angiogenic skin disorders such as psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

Diseases associated with neovascularization include optic disc neovascularization, iris neovascularization, retinal neovascularization, choroidal neovascularization, corneal neovascularization, and intravitreal neovascularization.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium.

Diseases associated with chronic inflammation and arthritis can be treated, ameliorated or prevented by the peptides, compositions and methods of the present invention. Diseases with symptoms of chronic inflammation include inflammatory bowel diseases such as Crohn's disease and ulcerative colitis, psoriasis, sarcoidosis, rheumatoid arthritis, osteoarthritis, lupus and scleroderma. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state.

Total daily dose of the peptides of the invention to be administered to a human or other mammal host in single or divided doses may be in amounts, for example, from about 0.0001 to about 750 mg/kg body weight daily and more usually about 1 to about 300 mg/kg body weight. In some embodiments, the pharmaceutical composition is administered by injections into the eye so that the peptide of the invention is given at a dose between about 0.1 mg and about 50 mg per injection, more preferably between about 0.3 and about 40 mg per injection, most preferably between about 0.5 mg and about 30 mg, about 1 mg and about 30 mg, about 3 mg and about 30 mg, about 5 mg and about 30 mg, about 8 mg and about 30 mg, about 10 mg and about 30 mg, about 15 mg and about 30 mg, about 20 mg and about 30 mg, about 0.5 mg and about 25 mg, about 0.5 mg and about 20 mg, about 0.5 mg and about 15 mg, about 0.5 mg and about 10 mg, about 0.5 mg and about 5 mg or about 0.5 mg and about 3 mg per injection. Further, the pharmaceutical composition is administered by eye drops to the eye so that a single drop of a solution containing a concentration of the peptide of the invention between about 10 and about 600 mg/ml, more preferably between about 20 and about 500 mg/ml, most preferably between about 30 and about 400 mg/ml, about 30 and about 350 mg/ml, about 30 and about 300 mg/ml, about 30 and about 250 mg/ml, about 30 and about 200 mg/ml, about 30 and about 150 mg/ml, about 30 and about 100 mg/ml, about 30 and about 50 mg/ml, about 50 and about 400 mg/ml, about 100 and about 400 mg/ml, about 150 and about 400 mg/ml, about 200 and about 400 mg/ml, about 250 and about 400 mg/ml, about 300 and about 400 mg/ml or about 350 and about 400 mg/ml is applied to the eye.

Administration of a therapeutically effective amount of pharmaceutical compositions of the present invention is defined as an amount effective, at dosages and for periods of time necessary to achieve the desired result. For example, a therapeutically active amount of a peptide may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

Pharmaceutical Compositions may be administered to subjects in need thereof via any convenient or suitable route such as by parenteral (including, for example, intraarterial, intravenous, intramuscular, subcutaneous), topical (including dermal, transdermal, subcutaneous, etc), oral, nasal, mucosal (including sublingual), or intracavitary routes. Thus compositions may be formulated in a variety of forms including solutions, suspensions, emulsions, and solid forms and are typically formulated so as to be suitable for the chosen route of administration, for example as an injectable formulations suitable for parenteral administration, capsules, tablets, caplets, elixirs for oral ingestion, in an aerosol form suitable for administration by inhalation (such as by intranasal inhalation or oral inhalation), or ointments, creams, gels, or lotions suitable for topical administration.

For example, pharmaceutical compositions for parenteral injection comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain adjuvants such as preservative, wetting agents, emulsifying agents, and dispersing agents.

For example, oral dosage forms or unit doses compatible for use with the peptides of the present invention may include a mixture of peptide, and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of the peptide, wherein the dosage form comprises at least one of a pill, a tablet, a capsule, a gel, a paste, a drink, and a syrup. In some instances, an oral dosage form is provided that is designed and configured to achieve delayed release of the peptide dimer in the subjects small intestine.

For example, topical administration includes administration to the skin or mucosa, including surfaces of the lung and eye. Compositions for topical lung administration, including those for inhalation and intranasal, may involve solutions and suspensions in aqueous and nonaqueous formulations and can be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour.

Peptides of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1 EMT Assay of the Peptides of the Invention

MDCK cells (800 cells/well) were seeded onto 96-well plate and incubated in 37° C. and 5% $CO_2$ to become 10% sub-confluence. Then EMT was triggered by adding culture medium with cell scattering factor HGF (R&D system, 2.5 ng/ml) and tested peptides were added (SEQ2~SEQ31) to block EMT. To measure the inter-nuclear distance, random images were captured at ×50 magnification using an upright microscope. The inter-nuclear distance was measured from the center of one nucleus to that of a neighboring/adjacent nucleus. The distance between the two nuclei was measured by using ImageJ software.

The peptides SEQ1 to SEQ11 are fragmented from an amino acid residue from position 500 to 604 of Dsg2, which is shown in below FIG. 1 (A). Moreover, EMT assay was conducted to demonstrate the EMT-inhibition ability of these peptide fragments. As shown in FIG. 1 (B), SEG6 shows advantageous effect in inhibiting EMT. Accordingly, a peptide deletion study was conducted for SEQ6. Synthetic peptides SEQ12 to SEQ 31 are obtained by deleting a portion of sequence of SEQ6. The sequences of the synthetic peptides SEQ12 to SEQ 31 and their inhibition effect on EMT are shown in FIG. 2.

Example 2 Vasculogenic Mimicry Study of the Peptides of the Invention

Human glioblastoma cells (U-87) were seeded on matrigel-coated well ($6\times10^3$ cells/well, in 96-well plate). Tested peptides (SEQ17, SEQ32-SEQ38 or PBS control) were then added into wells respectively and incubated for a few days. For quantification of tubes, each well was randomly photographed for three fields and the numbers of tubes were counted for statistics.

Figure 2:
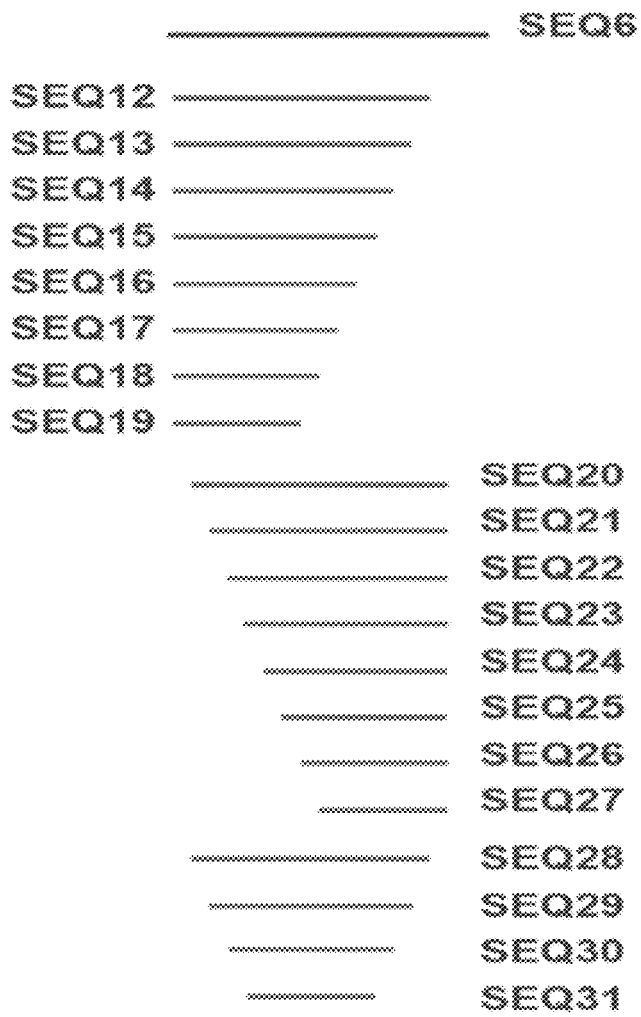
FIG. 2 (A) and (B) shows peptide deletion study of SEQ6 in EMT assay. (A), Schematic diagram of the SEQ6 deletion synthetic peptides SEQ12-SEQ31. Sequences of peptides SEQ12-SEQ31. (B), HGF (hepatocyte growth factor) induced EMT (epithelial-0.4-mesenchymal transition) was inhibited by synthetic peptides SEQ12-SEQ31. Moreover, SEQ15 and SEQ17 show excellent inhibiting abilities similar to SEQ6.
Figure 2:
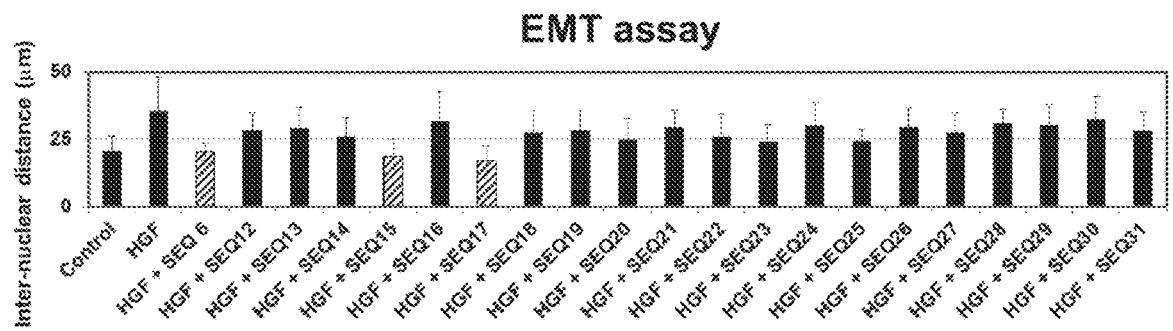
Figure 3:
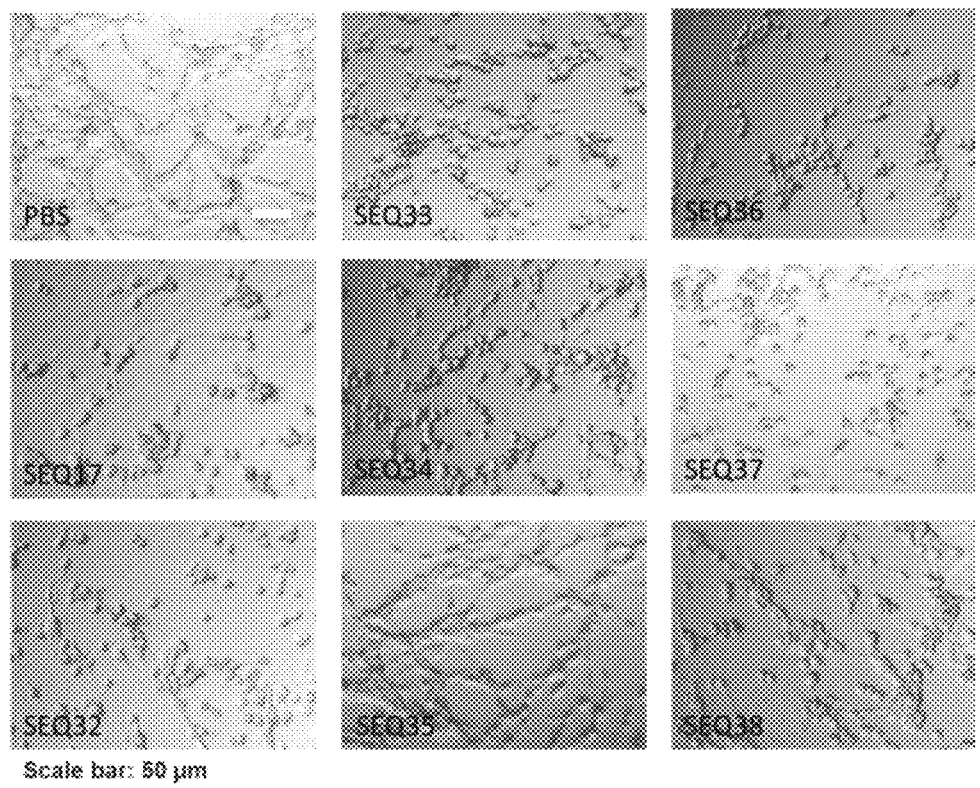
FIG. 3 (A) and (B) shows vasculogenic mimicry study using U87 cells determine the contribution of SEQ17 tryptophan residue (W, Dsg2 amino acid position 544) to the function of blocking tubes formation of U87 cells. SEQ32-SEQ38 are able to block vasculogenic mimicry. (A), Glioblastoma (GBM) is extremely aggressive and essentially incurable. Its malignancy is characterized by vigorous microvascular proliferations. Recent evidence has shown that tumor cells display the ability to drive blood-perfused vasculogenic mimicry (VM), an alternative microvascular circulation independent of endothelial cell angiogenesis. A glioblastoma cell line (U-87) is used to determine the contribution of SEQ17 tryptophan residue (W, Dsg2 amino acid position 544) through blocking matrigel triggered tube structure in vasculogenic mimicry study. Compared to PBS control of being full of tubes, peptides of SEQ17 and SEQ32-SEQ38 show strong efficacy to block U-87 tube networking. (B), Three randomly selected fields in each treatment group are used to quantitate by counting tubes. (average tube numbers±SD)
Figure 3:
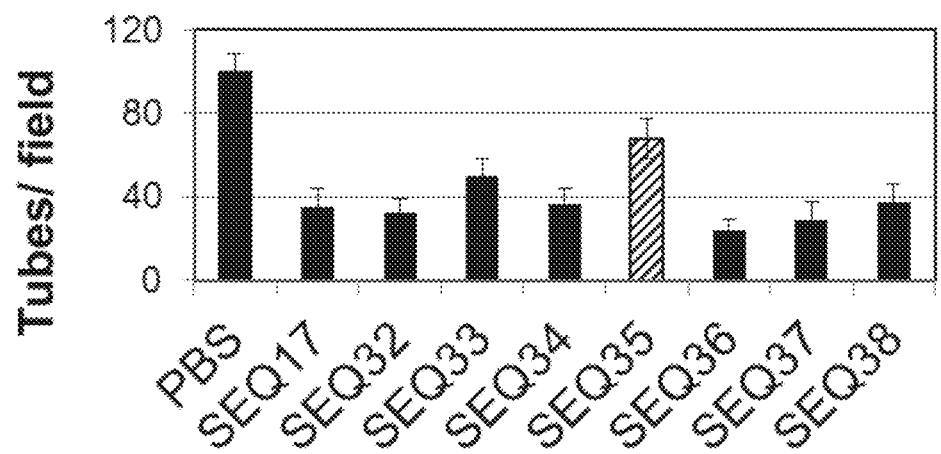

According to FIG. 2, SEQ17 shows an advantageous effect in the inhibition of EMT. An alanine screening of SEQ17 was conducted. Synthetic peptide sequences of SEQ32-SEQ38 obtained from alanine substitution synthetic peptides of SEQ17. Glioblastoma (GBM) is extremely aggressive and essentially incurable. Its malignancy is characterized by vigorous microvascular proliferations. Recent evidence has shown that tumor cells display the ability to drive blood-perfused vasculogenic mimicry (VM), an alternative microvascular circulation independent of endothelial cell angiogenesis. A glioblastoma cell line (U-87) is used to determine the contribution of SEQ17 tryptophan residue (W, Dsg2 amino acid position 544) through blocking matrigel triggered tube structure in vasculogenic mimicry study. Compared to PBS control of being full of tubes, peptides of SEQ17 and SEQ32-SEQ38 show strong efficacy to block U-87 tube networking (see FIG. 3 (A)). Three randomly selected fields in each treatment group are used to quantitate by counting tubes (see FIG. 3 (B)). (average tube numbers±SD)

Figure 4:
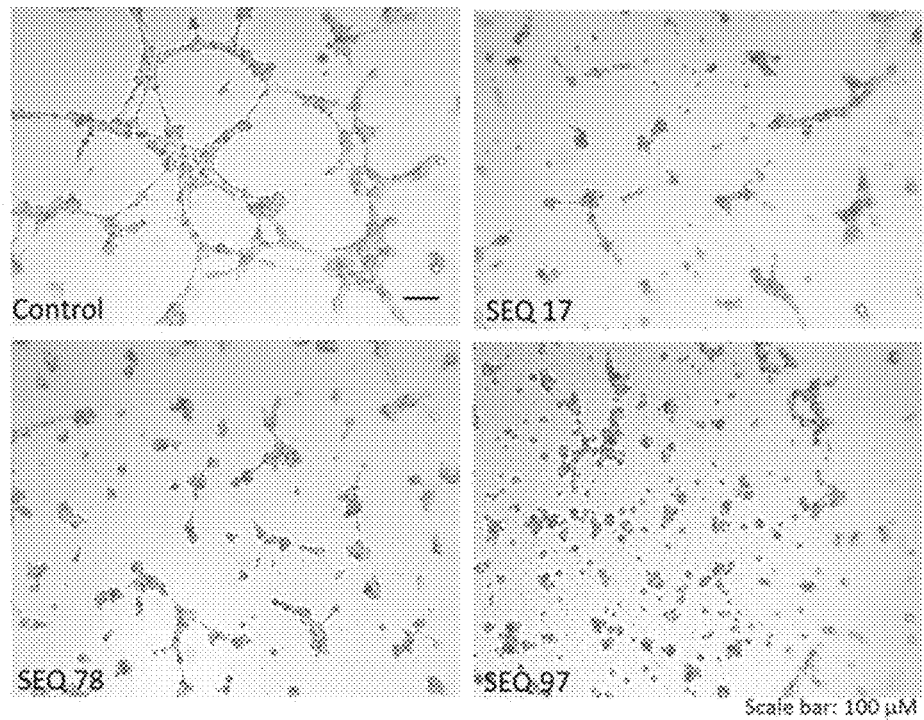
FIGS. 4 (A) to (D) shows HUVEC tube formation assay of the peptides of the invention. (A), HUVEC cells cultured on Matrigel demonstrate that the synthetic peptides SEQ17, SEQ78, and SEQ97 inhibit angiogenesis. (B), MR9 and three peptides derived from MR9 (MR9; MR9 DF: non-nature amino acid peptide, 9 amino acid residues are D form; CMR9C: cyclic peptide, cyclization by N and C terminal Cystines; and CMR9C DF: cyclic peptide with non-nature amino acids) are treated to matrigel-induced vasculature of HUVEC cells. These peptides can show potential capability to break down tube structure 40%-80%. (C), The SEQ132 peptide, a reverse sequence of SEQ6, shows strong efficacy to inhibit HUVEC tube structure in the HUVEC tube formation assay. (D), MR9D6 and two peptides derived from MR9D6 (MR9D6; MR9D6 DF: non-nature amino acid peptide, 15 amino acid residues are D form; and CMR9D6C DF: cyclic peptide, cyclization by N and C terminal Cystines, and all amino acids are non-natural D-form) are treated to matrigel induced vasculature of HUVEC cells. These PBS-dissolved peptides can show extremely efficacious ability to collapse 95% volume of tube structure compared to PBS-treated control.
Figure 4:
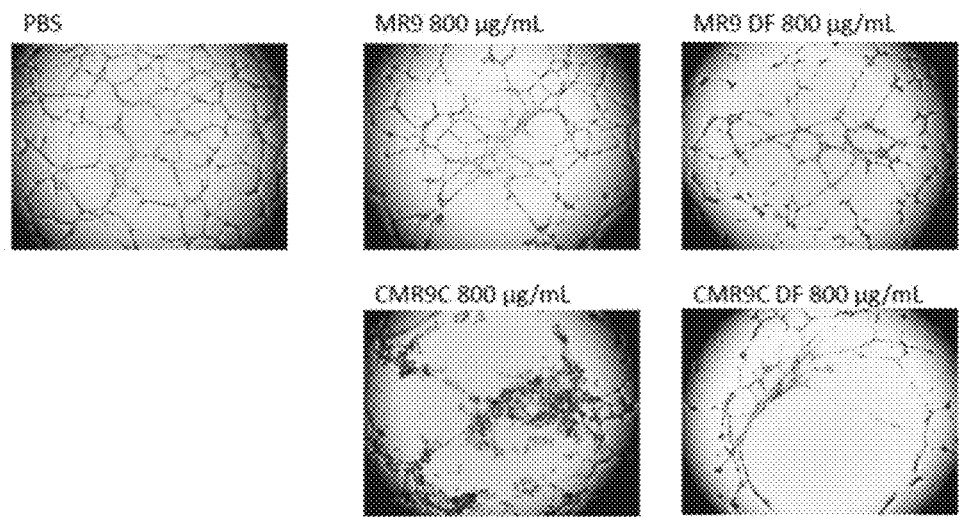
Figure 4:
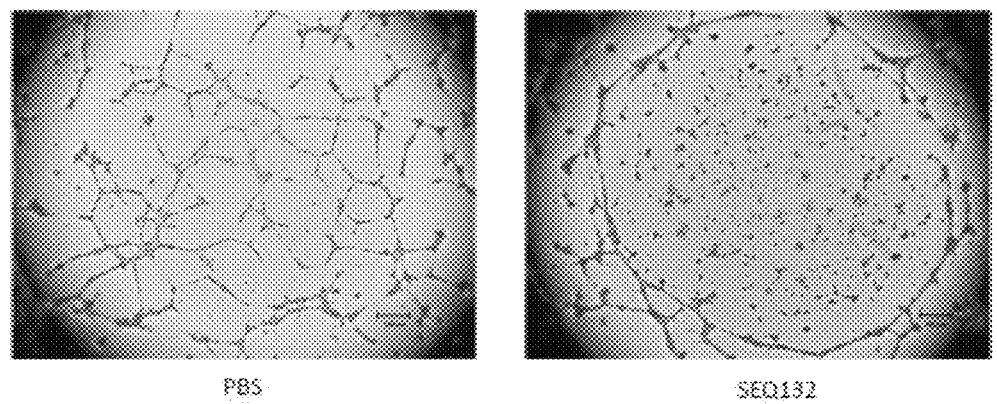
Figure 4:
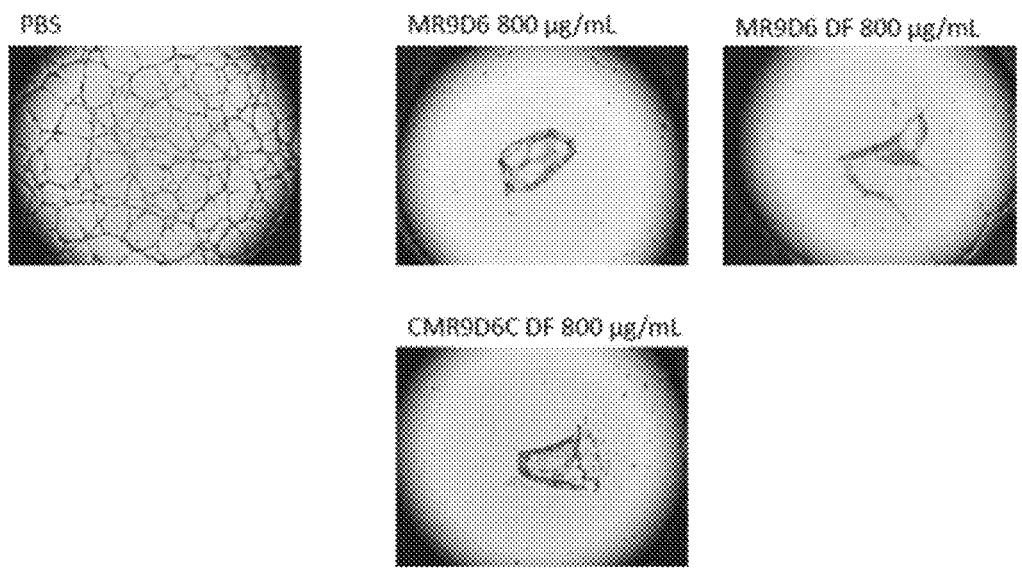

Example 3 HUVEC Tube Formation Assay (Angiogenesis Assay) of the Peptides of the Invention Overnight starved human umbilical vein endothelial cells (HUVEC) were collected and adjusted to $1.5\times10^4$ cells/well (in a 96-well plate) with endothelial cell growth medium and then seeded cells on the matrigel-coated well. Different peptides and their modified forms by D-form non-nature amino acids and/or cyclization by adding N- and C-terminal Cystines; also SEQ132 is a reversal of the direction of the peptide backbone SEQ6 (retro modification): (SEQ17, SEQ78, SEQ97, MR9 DF, CMR9C, CMR9C DF, MR9D6 DF, CMR9D6C DF and SEQ132) or control PBS were added into well for five-hour incubation at 37° C. Each well was photographed at ×40 magnification through an upright microscope. Total tube lengths were quantified by using ImageJ software. HUVEC cells cultured on matrigel demonstrate that the synthetic peptides can inhibit angiogenesis and the results are shown in FIGS. 4 (A) to (D).

Example 4 Rat Laser-Induced Choroidal Neovascularization Model

The animals were fully anesthetized with a mixture of ketamine hydrochloride/xylazine hydrochloride (7:1, v/v) by intramuscular injection into the thigh muscle at 1 mL/kg. Mydrin®-P ophthalmic solution (Santen Pharmaceutical Co., Ltd.) was instilled into the eyes to dilate the pupils.

Laser (wavelength: 532 nm) was used to irradiate the right eye of each animal using a Slit Lamp SL-130 (Carl Zeiss Meditec AG) and a Multicolor Laser Photocoagulator MC-300 (NIDEK Co., Ltd.). Then the peptide dosing formulation was injected into the vitreous body of the right eye using a microsyringe (MS-N10, Ito Corporation) and a 33 G needle (Ito Corporation). Fourteen days after laser irradiation, a 4% FITC-dextran solution was administered into the tail vein in a volume of 1 mL/animal. Then the animals were euthanized by overdose of an anesthetic. The eyeballs were removed and fixed in 4% paraformaldehyde-phosphate buffer for 12-24 hours. Choroidal flat mounts were prepared under a stereoscopic microscope (EZ-4, Leica Microsystems). The rat eye choroidal flat mounts were then prepared for photographing by a confocal microscope (NIKON ECLIPSE TE2000-U). Software ImageJ (National Institutes of Health (NIH), USA) will be used to measure the area of laser-induced neovascularization site (unit: pixel) with high fluorescein intensity.

Figure 5:
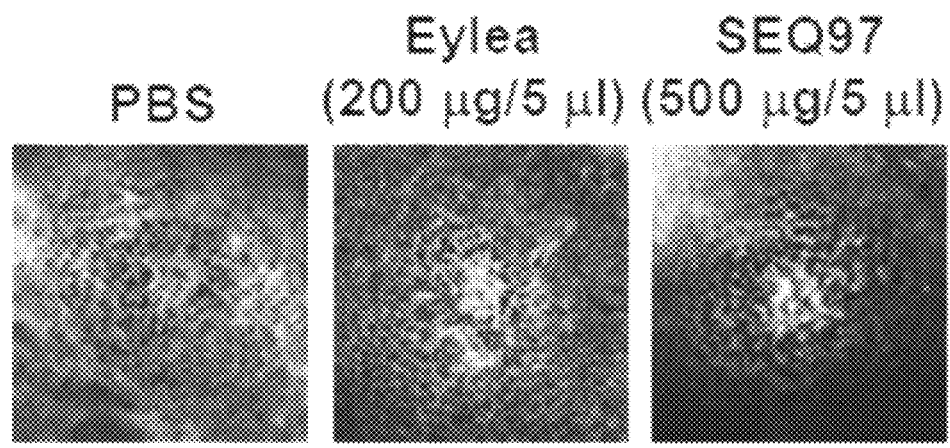
FIG. 5 (A) and (B) shows the animal model investigation (rat choroidal neovascularization model. (A), Fluorescein angiography photos of PBS-treated control, Eylea (200 µg/5 µl) and SEQ97 500 µg/5 µl). (B), Eylea and SEQ97 significantly inhibit rat eyes choroidal neovascularization.
Figure 5:
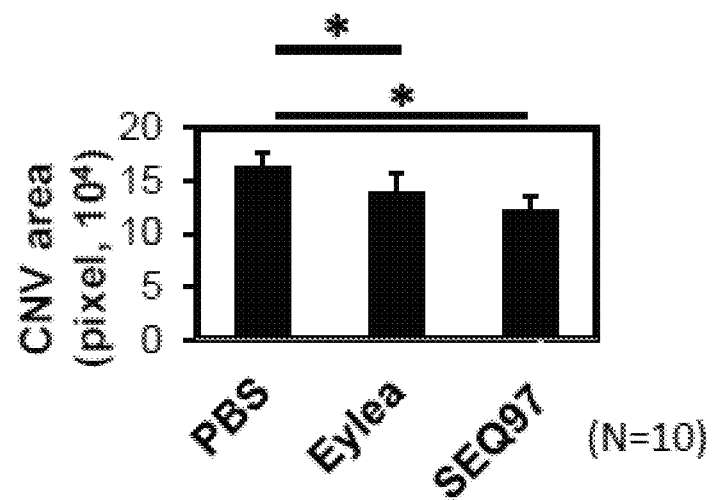

Eyes of rats were irradiated by 532 nm wave length laser and intraveally treated with peptides (SEQ97), Eylea or PBS. 14 days later, a 4% FITC-dextran solution would be then intravenously injected to identify the leakage of fluid in the retina area through fluorescein angiography. FIG. 5 (A) shows the fluorescein angiography photos of PBS-treated control, Eylea (200 μg/5 μl) and SEQ97 500 μg/5 μl). After treatment (PBS, Eylea or SEQ97) for 14 days, the photographs of the choroidal neovascularization sites were taken and quantified with ImageJ software. (n=10) Both Eylea and SEQ97 significantly inhibit rat eyes choroidal neovascularization (see FIG. 5 (B)). (Statistical analysis was using StatLight #4)

We claim:

1. A synthetic peptide comprising an amino acid sequence selected from the group consisting of the following:

| | | |
|---|---|---|
| SEQ32 | AAEKWKIAR | (SEQ ID NO: 38) |
| SEQ33 | MAAKWKIAR | (SEQ ID NO: 39) |
| SEQ34 | MAEAWKIAR | (SEQ ID NO: 40) |
| SEQ35 | MAEKAKIAR | (SEQ ID NO: 41) |
| SEQ36 | MAEKWAIAR | (SEQ ID NO: 42) |
| SEQ37 | MAEKWKAAR | (SEQ ID NO: 43) |
| SEQ38 | MAEKWKIAA | (SEQ ID NO: 44) | or a variant peptide thereof having one or two conservative substitutions thereof,
or cyclical modified peptides thereof,
or peptides having a homopolyamino acid sequence at the N-, C-, or both N- and C-terminus thereof wherein the homopolyamino acid sequence is a peptide having from 1 to 12 amino acids and comprises a contiguous repeat of one of K, D, R, E, or Q.

2. A synthetic peptide comprising an amino acid sequence selected from the group consisting of the following:
MAEKWKIAR (SEQ ID NO:64) wherein at least one of the amino acid residues are of the stereochemical D-form;

| | |
|---|---|
| CMAEKWKIARC; | (SEQ ID NO: 65) |
| MAEKWKIARDDDDDD; and | (SEQ ID NO: 66) |
| CMAEKWKIARDDDDDC | (SEQ ID NO: 67), | or a variant peptide thereof having one or two conservative substitutions thereof,
or cyclical modified peptides thereof,
or peptides having a homopolyamino acid sequence at the N-, C-, or both N- and C-terminus thereof wherein the homopolyamino acid sequence is a peptide having from 1 to 12 amino acids and comprises a contiguous repeat of one of K, D, R, E, or Q.

3. A synthetic peptide comprising an amino acid sequence selected from the group consisting of:

| | |
|---|---|
| CMAEKWKIARC; and | (SEQ ID NO: 65) |
| CMAEKWKIARDDDDDC | (SEQ ID NO: 67). |

4. A synthetic peptide comprising an amino acid sequence selected from the group consisting of:

| | | |
|---|---|---|
| SEQ74 | RRRMAEKWKIAR | (SEQ ID NO: 68) |
| SEQ75 | RRRRMAEKWKIAR | (SEQ ID NO: 69) |
| SEQ76 | RRRRRMAEKWKIAR | (SEQ ID NO: 70) |
| SEQ77 | RRRRRRMAEKWKIAR | (SEQ ID NO: 71) |
| SEQ78 | RRRRRRRMAEKWKIAR | (SEQ ID NO: 72) |
| SEQ79 | MAEKWKIARDDD | (SEQ ID NO: 73) |
| SEQ80 | RRRMAEKWKIARDDD | (SEQ ID NO: 74) |
| SEQ81 | RRRRMAEKWKIARDDD | (SEQ ID NO: 75) |
| SEQ82 | RRRRRMAEKWKIARDDD | (SEQ ID NO: 76) |
| SEQ83 | RRRRRRMAEKWKIARDDD | (SEQ ID NO: 77) |
| SEQ84 | RRRRRRRMAEKWKIARDDD | (SEQ ID NO: 78) |
| SEQ85 | MAEKWKIARDDDD | (SEQ ID NO: 79) |
| SEQ86 | RRRMAEKWKIARDDDD | (SEQ ID NO: 80) |
| SEQ87 | RRRRMAEKWKIARDDDD | (SEQ ID NO: 81) |
| SEQ88 | RRRRRMAEKWKIARDDDD | (SEQ ID NO: 82) |
| SEQ89 | RRRRRRMAEKWKIARDDDD | (SEQ ID NO: 83) |
| SEQ90 | RRRRRRRMAEKWKIARDDDD | (SEQ ID NO: 84) |
| SEQ91 | MAEKWKIARDDDDD | (SEQ ID NO: 85) |
| SEQ92 | RRRMAEKWKIARDDDDD | (SEQ ID NO: 86) |
| SEQ93 | RRRRMAEKWKIARDDDDD | (SEQ ID NO: 87) |

```
                          -continued
SEQ94      RRRRRMAEKWKIARDDDDD       (SEQ ID NO: 88)
SEQ95      RRRRRRMAEKWKIARDDDDD      (SEQ ID NO: 89)
SEQ96      RRRRRRRMAEKWKIARDDDDD     (SEQ ID NO: 90)
SEQ97      MAEKWKIARDDDDDD           (SEQ ID NO: 91)
SEQ98      RRRMAEKWKIARDDDDDD        (SEQ ID NO: 92)
SEQ99      RRRRMAEKWKIARDDDDDD       (SEQ ID NO: 93)
SEQ100     RRRRRMAEKWKIARDDDDDD      (SEQ ID NO: 94)
SEQ101     RRRRRRMAEKWKIARDDDDDD     (SEQ ID NO: 95)
SEQ102     RRRRRRRMAEKWKIARDDDDDD    (SEQ ID NO: 96)
SEQ103     DDDMAEKWKIAR              (SEQ ID NO: 97)
SEQ104     DDDDMAEKWKIAR             (SEQ ID NO: 98)
SEQ105     DDDDDMAEKWKIAR            (SEQ ID NO: 99)
SEQ106     DDDDDDMAEKWKIAR           (SEQ ID NO: 100)
SEQ107     MAEKWKIARRRR              (SEQ ID NO: 101)
SEQ108     DDDMAEKWKIARRRR           (SEQ ID NO: 102)
SEQ109     DDDDMAEKWKIARRRR          (SEQ ID NO: 103)
SEQ110     DDDDDMAEKWKIARRRR         (SEQ ID NO: 104)
SEQ111     DDDDDDMAEKWKIARRRR        (SEQ ID NO: 105)
SEQ112     MAEKWKIRRRRRR             (SEQ ID NO: 106)
SEQ113     DDDMAEKWKIARRRRR          (SEQ ID NO: 107)
SEQ114     DDDDMAEKWKIARRRRR         (SEQ ID NO: 108)
SEQ115     DDDDDMAEKWKIARRRRR        (SEQ ID NO: 109)
SEQ116     DDDDDDMAEKWKIARRRRR       (SEQ ID NO: 110)
SEQ117     MAEKWKIARRRRRR            (SEQ ID NO: 111)
SEQ118     DDDMAEKWKIARRRRRR         (SEQ ID NO: 112)
SEQ119     DDDDMAEKWKIARRRRRR        (SEQ ID NO: 113)
SEQ120     DDDDDMAEKWKIARRRRRR       (SEQ ID NO: 114)
SEQ121     DDDDDDMAEKWKIARRRRRR      (SEQ ID NO: 115)
SEQ122     MAEKWKIARRRRRRR           (SEQ ID NO: 116)
SEQ123     DDDMAEKWKIARRRRRRR        (SEQ ID NO: 117)
SEQ124     DDDDMAEKWKIARRRRRRR       (SEQ ID NO: 118)
SEQ125     DDDDDMAEKWKIARRRRRRR      (SEQ ID NO: 119)
SEQ126     DDDDDDMAEKWKIARRRRRRR     (SEQ ID NO: 120)
SEQ127     MAEKWKIARRRRRRRR          (SEQ ID NO: 121)
SEQ128     DDDMAEKWKIARRRRRRRR       (SEQ ID NO: 122)
SEQ129     DDDDMAEKWKIARRRRRRRR      (SEQ ID NO: 123)
SEQ130     DDDDDMAEKWKIARRRRRRRR     (SEQ ID NO: 124)
SEQ131     DDDDDDMAEKWKIARRRRRRRR    (SEQ ID NO: 125).
```

5. A synthetic peptide having the sequence of any of SEQ ID NO: 68 to SEQ ID NO: 125, wherein the peptide further comprises one or two non-naturally occurring amino acid modifications at the N-, C-, or both N- and C-terminus, wherein the non-naturally occurring amino acid modifications are selected from: azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline.

6. A synthetic peptide having the sequence of any of SEQ ID NO: 68 to SEQ ID NO: 125, wherein the peptide is in a cyclic form.

7. A synthetic peptide comprising an amino acid sequence of VSTSEQRAIKWKEAM (SEQ ID NO:136).

8. A pharmaceutical composition comprising a peptide of any of claims 1, 2-3, or 4-6.

9. A method of inhibiting EMT and/or vasculogenic mimicry for treating or preventing an EMT associated disease in a subject, comprising administering to said subject a therapeutically effective amount of an amino acid sequence of formula (I) to the subject $$MX_1EX_2WX_3IX_4R \quad \text{(SEQ ID NO: 1)} \quad (I)$$

wherein $X_1$ is A or T;

$X_2$ is K or R;

$X_3$ is K, R or N; and $X_4$ is A, V or I or a variant peptide thereof having one or two conservative substitutions thereof, or cyclical modified peptides thereof, or peptides having a homopolyamino acid sequence at the N-, C-, or both N- and C-terminus thereof wherein the homopolyamino acid sequence is a peptide having from 1 to 12 amino acids and comprises a contiguous repeat of one of K, D, R, E, or Q.

10. The method of claim 9, wherein the peptide or the peptide variant or the modified peptide thereof is administered via a parenteral, topical or oral route.

11. The method of claim 10, wherein the topical administration is to the eye.

12. The method of claim 9, wherein the EMT associated disease is neoplasia, macular degeneration, vascular retinopathy or retinal degeneration, wherein the neoplasia is selected from a malignant tumor or cancer selected from: glioblastoma, cervical cancer, anal cancer, oral cancer, stomach cancer, colon cancer, bladder cancer, rectal cancer, liver cancer, pancreatic cancer, lung cancer, breast cancer, cervix uteri cancer, corpus uteri cancer, ovary cancer, prostate cancer, testis cancer, renal cancer, brain cancer, head and neck cancer, eye cancer or ocular cancer, throat cancer, melanoma, Ewing's Sarcoma, Kaposi's Sarcoma, basal cell carcinoma, squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, kidney cancer and lymphoma.

13. The method of claim 9, wherein the EMT associated disease is selected from: psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, and inflammation.

14. The method of claim 9, wherein the EMT associated disease is selected from: optic disc neovascularization, iris neovascularization, retinal neovascularization, choroidal neovascularization, corneal neovascularization, and intravitreal neovascularization.

15. The method of claim 9, wherein the EMT associated disease is ocular neovascular disease or macular degeneration.

16. The method of claim 9, wherein the macular degeneration is age-related macular degeneration.

17. The synthetic peptide of claim 1, wherein the variant peptide has one or two conservative substitutions.

18. The synthetic peptide of claim 1, wherein the modified peptide is a cyclical modified peptide.

19. The synthetic peptides of claim 2, wherein the variant peptide has one or two conservative substitutions.

20. The method of claim 9, wherein the modified peptide comprises a variant peptide having one or two conservative substitutions.

21. The method of claim 9, wherein the peptide has a cyclic modification.

22. The method of claim 12, wherein the cancer is selected from breast cancer, prostate cancer, color cancer, basal cell carcinoma, bladder cancer, and glioblastoma.

23. A synthetic peptide of claim 1, consisting of an amino acid sequence of SEQ ID NO: 38-44.

24. A synthetic peptide of claim 2, consisting of an amino acid sequence of SEQ ID NO: 65-67.

* * * * *